United States Patent
Kanou

(10) Patent No.: US 10,113,975 B2
(45) Date of Patent: Oct. 30, 2018

(54) APPEARANCE INSPECTION DEVICE AND METHOD FOR OBJECT HAVING LINE PATTERN

(71) Applicant: FANUC CORPORATION, Yamanashi (JP)

(72) Inventor: Rui Kanou, Yamanashi (JP)

(73) Assignee: FANUC CORPORATION, Yamanashi (JP)

(*) Notice: Subject to any disclaimer, the term of this patent is extended or adjusted under 35 U.S.C. 154(b) by 421 days.

(21) Appl. No.: 14/192,109

(22) Filed: Feb. 27, 2014

(65) Prior Publication Data

US 2014/0240488 A1    Aug. 28, 2014

(30) Foreign Application Priority Data

Feb. 28, 2013 (JP) ................. 2013-039416

(51) Int. Cl.
    *G01N 21/88*    (2006.01)
    *G01N 21/956*   (2006.01)
    *G06T 7/00*     (2017.01)

(52) U.S. Cl.
    CPC ....... *G01N 21/8803* (2013.01); *G01N 21/956* (2013.01); *G06T 7/001* (2013.01); *G06T 2207/20081* (2013.01); *G06T 2207/30152* (2013.01)

(58) Field of Classification Search
    None
    See application file for complete search history.

(56) References Cited

U.S. PATENT DOCUMENTS

| 6,687,398 B1 | 2/2004 | Kriwet et al. |
| 7,559,047 B2 * | 7/2009 | Miyamoto .......... G03F 7/70625 382/144 |
| 2006/0140471 A1 | 6/2006 | Murakami et al. |

(Continued)

FOREIGN PATENT DOCUMENTS

| CN | 1797426 A | 7/2006 |
| CN | 101086481 A | 12/2007 |

(Continued)

OTHER PUBLICATIONS

Machine translation of Japanese Patent Publication No. 63-206877 and human translation of drawings.*

(Continued)

*Primary Examiner* — Kate H Luo
(74) *Attorney, Agent, or Firm* — Hauptman Ham, LLP

(57) ABSTRACT

An appearance inspection device and an appearance inspection method, capable of teaching a line pattern having an arbitrary shape as a portion to be inspected, in relation to a captured image of an inspection object, by a simple teaching operation. The device has an image storing part, a teaching part, an inspecting part and an inspection factor storing part. The teaching part obtains an image of the inspection object in the teaching process, and teaches the position of an inspection point, the position and the angle of an inspection region relative to the inspection point, the inspection factor and a judgment condition. The teaching factor storing part stores a setting parameter and a teaching factor. The inspecting part executes inspection based on the teaching factor in the inspecting process.

18 Claims, 22 Drawing Sheets

(56) References Cited

U.S. PATENT DOCUMENTS

| | | |
|---|---|---|
| 2008/0040058 A1 | 2/2008 | Fujii et al. |
| 2009/0097735 A1* | 4/2009 | Sasajima ............... G06T 7/001 382/141 |
| 2009/0202140 A1* | 8/2009 | Mitsui ................. G06K 9/4604 382/145 |
| 2009/0218491 A1* | 9/2009 | Morokuma ............ G01B 15/04 250/310 |
| 2010/0158389 A1* | 6/2010 | Mitsui ................. G03F 7/7065 382/199 |
| 2010/0196804 A1* | 8/2010 | Murakawa ............... G03F 1/86 430/5 |
| 2010/0220910 A1 | 9/2010 | Kaucic et al. |
| 2012/0105617 A1* | 5/2012 | Yoon ...................... G06T 7/60 348/80 |
| 2012/0141013 A1* | 6/2012 | Gao ..................... G06T 7/001 382/149 |
| 2012/0294507 A1* | 11/2012 | Sakai .................. G01N 21/956 382/149 |
| 2012/0327212 A1* | 12/2012 | Kitahashi ............... H01J 37/28 348/80 |

FOREIGN PATENT DOCUMENTS

| | | |
|---|---|---|
| CN | 101122569 A | 2/2008 |
| DE | 19713521 B4 | 9/2004 |
| JP | 63206877 A | 8/1988 |
| JP | 08-334478 A | 12/1996 |
| JP | 11-037724 A | 2/1999 |
| JP | 2003-086996 A | 3/2003 |
| JP | 200469698 A | 3/2004 |
| JP | 2010-054289 A | 3/2010 |
| JP | 201195226 A | 5/2011 |

OTHER PUBLICATIONS

Kunihiko Hattori, "Visual Deficiency Inspection Device PLX-1000—Application of Line Sensor Camera—", A Monthly Journal of Imaging and Information Technology, Sangyo Kaihatsukiko Inc., Jun. 1, 1999, vol. 31, No. 11, pp. 31-37.

Office Action dated Jul. 29, 2014, corresponds to Japanese patent application No. 2013-039416.

* cited by examiner

APPEARANCE INSPECTION DEVICE AND METHOD FOR OBJECT HAVING LINE PATTERN

RELATED APPLICATIONS

The present application claims priority to Japanese Application Number 2013-039416, filed Feb. 28, 2013, the disclosure of which is hereby incorporated by reference herein in its entirety.

BACKGROUND OF THE INVENTION

1. Field of the Invention

The present invention relates to a device and a method for carrying out appearance inspection of an object having a line pattern, and in particular, relates an appearance inspection device and an appearance inspection method, wherein the object is captured by a camera and it is judged as to whether an appearance of the object is good or not by using obtained image data of the object.

2. Description of the Related Art

In the prior art, in an assembly process of various components, a state of a sealing agent or adhesive is usually inspected after the agent or adhesive is applied to a surface of a component to be bonded. This inspection may be carried out by an operator visually, or by an inspection device having an image processing function. As a factor to be inspected, color, brightness, an area and/or a width of the applied adhesive may be evaluated. If the inspection is carried out by using an image, when the brightness or the width of a specified portion should be inspected, an inspection region surrounding the portion may be determined. In this case, it is not difficult to teach the factor to be inspected to the inspection device.

However, the sealing agent or adhesive is applied to the component in various shapes (in many cases, in an elongated line pattern) corresponding to a shape of the component, it is difficult to teach where in the sealing agent should be inspected and how the sealing agent should be inspected. Even when the shape of a portion to be inspected can be taught, it may be difficult to teach how the portion should be inspected. In addition, when a teaching method is specified as a particular inspection (for example, an inspection of the width), it is often difficult to carry out another inspection (for example, an inspection of the brightness).

As an inspection of a line pattern such as a sealing agent, etc., by using image processing, there are some well-known techniques. For example, JP 2010-054289A discloses a method for judging continuity of a line pattern, wherein the line pattern is captured; a captured image is digitalized so as to separate the line pattern from the other region and detect a profile of the line pattern; and the profile is traced by determining an edge point positioned at one end of both ends within an inspection object range, as a start point.

JP H08-334478 A discloses a seal inspection system having a specification function for inspecting the position of an image of an inspection width portion corresponding to a seal application position; and a function for judging the positions of two pixels where a change in concentration exceeds a set value, among pixels from both end positions to an inspection position in relation to an inspection width in image data, as both ends (or edges) of the sealing agent in the width direction thereof.

JP H11-037724 A discloses a method including: approximating a captured image of a sealing agent by a polygonal line; dividing the sealing agent into a plurality of portions based on a coordinate of each edge of the polygonal line; providing windows to the divided portions; and detecting the width and position of the seal portions within each window.

It may be difficult to apply the method in JP 2010-054289 A to a case wherein a contrast between the line pattern and a background thereof is not clear. On the other hand, in the method of JP H08-334478 A, since both the brightness and the width of the sealing agent cannot be simultaneously inspected at the inspection point, even the sealing agent offset from a predetermined position may be judged as "success." Further, JP H08-334478 does not describe a method for setting the inspection point.

In the method of JP H11-037724 A, in fact, success/failure of the inspection depends on whether a line pattern is correctly extracted from an image and is approximate by a polygonal line. Therefore, depending on an object to be inspected, it may be impossible to inspect the object, or inspection criteria may be varied. Further, the calculation for extracting the line pattern and approximating it by a polygonal line is costly and takes a lot of time. In addition, JP H11-037724 does not describe a case wherein a line pattern of an object to be inspected includes a branch point, and thus the method of this document is difficult to be applied to a line pattern having an arbitrary shape.

SUMMARY OF THE INVENTION

An object of the present invention is to provide an appearance inspection device and an appearance inspection method, capable of teaching a line pattern having an arbitrary shape (including a branch point) as a portion to be inspected, in relation to a captured image of an object to be inspected, by a simple teaching operation.

According to one aspect of the present invention, an appearance inspection device for inspecting an appearance of an inspection object is provided, the device comprising: an image storing part which stores a first image obtained by capturing a reference object corresponding to the inspection object and a second image obtained by capturing the inspection object; a teaching part which teaches, on the first image, a portion to be inspected of the inspection object as a reference inspection line, defines a reference inspection region associated with one reference inspection point on the inspection reference line, determines an inspection factor inspected within the reference inspection region, and determines a judgment condition for judging as to whether a result of inspection based on the inspection factor passes or fails; a teaching factor storing part which stores a position and a shape of the reference inspection line, a position of the reference inspection point, a position and a size of the reference inspection region, the inspection factor and the judgment condition; and an inspecting part which overlaps the reference inspection line on the second image as an actual inspection line, generates a plurality inspection points on the actual inspection line, generates an inspection region in relation to each inspection point so that a positional relationship between the inspection point and the inspection region is the same as a positional relationship between the reference inspection point and the reference inspection region, inspects each of generated inspection regions based on the inspection factor, judges as to whether each inspection point passes or fails based on the judgment condition in relation to a result of executed inspection, and comprehensively judges as to whether the inspection object passes or fails based on a result of judgment of each inspection point.

In a preferred embodiment, the teaching part teaches the reference inspection line using one of a polygonal line, an arc, a circle and a free curve, or a combination thereof.

In a preferred embodiment, the teaching factor storing part stores a position of the reference object within the first image, and the inspecting part generates the plurality inspection points after moving the actual inspection line so that a position of the actual inspection line relative to a position of the inspection object within the second image is the same as a position of the reference inspection line relative to the reference object stored in the teaching factor storing part.

In a preferred embodiment, the teaching part defines a plurality of reference inspection regions associated with the reference inspection point and determines an inspection factor in relation to each reference inspection region, and the inspecting part inspects a plurality of inspection regions generated corresponding to the plurality of reference inspection regions based on the inspection factor, and the inspection part applies the judgment condition to a result of inspection in each of the plurality of inspection regions so as to obtain the result of judgment of each inspection point.

In a preferred embodiment, the plurality of inspection points are generated, at predetermined regular intervals, on the actual inspection line overlapped with the second image.

According to another aspect of the present invention, an appearance inspection method for inspecting an appearance of an inspection object is provided, the method comprising: an image storing process for storing a first image obtained by capturing a reference object corresponding to the inspection object and a second image obtained by capturing the inspection object; a teaching process for teaching, on the first image, a portion to be inspected of the inspection object as a reference inspection line, defining a reference inspection region associated with one reference inspection point on the inspection reference line, determining an inspection factor inspected within the reference inspection region, and determining a judgment condition for judging as to whether a result of inspection based on the inspection factor passes or fails; a teaching factor storing process for storing a position and a shape of the reference inspection line, a position of the reference inspection point, a position and a size of the reference inspection region, the inspection factor and the judgment condition; and an inspecting process for overlapping the reference inspection line on the second image as an actual inspection line, generating a plurality inspection points on the actual inspection line, generating an inspection region in relation to each inspection point so that a positional relationship between the inspection point and the inspection region is the same as a positional relationship between the reference inspection point and the reference inspection region, inspecting each of generated inspection regions based on the inspection factor, judging as to whether each inspection point passes or fails based on the judgment condition in relation to a result of executed inspection, and comprehensively judging as to whether the inspection object passes or fails based on a result of judgment of each inspection point.

In a preferred embodiment, the teaching process includes teaching the reference inspection line using one of a polygonal line, an arc, a circle and a free curve, or a combination thereof.

In a preferred embodiment, the teaching factor storing process includes storing a position of the reference object within the first image, and the inspecting process includes generating the plurality inspection points after moving the actual inspection line so that a position of the actual inspection line relative to a position of the inspection object within the second image is the same as a position of the reference inspection line relative to the reference object stored in the teaching factor storing part.

In a preferred embodiment, the teaching process includes defining a plurality of reference inspection regions associated with the reference inspection point and determining an inspection factor in relation to each reference inspection region, and the inspecting process includes inspecting a plurality of inspection regions generated corresponding to the plurality of reference inspection regions based on the inspection factor, and applying the judgment condition to a result of inspection in each of the plurality of inspection regions so as to obtain the result of judgment of each inspection point.

In a preferred embodiment, the plurality of inspection points are generated, at predetermined regular intervals, on the actual inspection line overlapped with the second image.

BRIEF DESCRIPTION OF THE DRAWINGS

The above and other objects, features and advantages of the present invention will be made more apparent by the following description of the preferred embodiments thereof with reference to the accompanying drawings wherein:

FIG. 3b shows a state wherein adhesive agent is appropriately applied to the inspection object of FIG. 3a;

FIG. 3c shows a state wherein adhesive agent is inappropriately applied to the inspection object of FIG. 3a;

DETAILED DESCRIPTION

Figure 1:
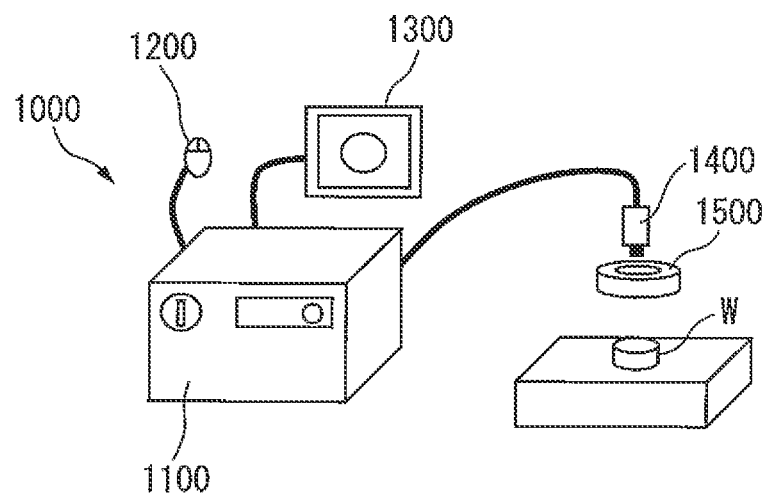
FIG. 1 is a view of a schematic configuration of a system including an appearance inspection device according to an embodiment of the present invention.

FIG. 1 shows a total configuration of a system 1000 including an appearance inspection device according to the present invention. System 1000 includes an appearance inspection device 1100, an operation device 1200, a display device 1300, a capture device 1400 and an illumination device 1500. Appearance inspection device 1100 is capable of teaching a portion of an inspection object W to be inspected, teaching an inspection factor of the appearance inspection, executing inspection based on the taught inspection factor, and outputting a result of the executed inspection. Appearance inspection device 1100 may be a specialized device for the appearance inspection, otherwise, may be a generalized personal computer or workstation.

Operation device 1200 is connected to appearance inspection device 1100 and is configured to allow an operator to input information or a command regarding the inspection into appearance inspection device 1100. Operation device 1200 may be a generalized device such as a mouse, a keyboard, a pointing device, a touch panel, a button or a switch, etc.

Display device 1300 is connected to appearance inspection device 1100 and is configured to display a setting parameter which is set in appearance inspection device 1100 by using operation device 1200, an operating status of appearance inspection device 1100, an image used for the inspection, and a result of inspection, etc. Display device 1300 may be a specialized device for appearance inspection device 1100, otherwise, may be a generalized device such as a liquid-crystal display, a CRT display, or an organic light emitting display, etc. In addition, like a touch panel, operation device 1200 and display device 1300 may be integrally constituted.

Capture device 1400 is used to obtain an image of inspection object W, and may be configured to obtain an image of a reference inspection object (described below), as well as inspection object W. Typically, capture device 1400 is an industrial camera such as a CCD camera or a CMOS camera. Otherwise, capture device 1400 may be a line sensor camera, an infrared camera, an ultraviolet camera, or a range image sensor. In addition, when a camera is used as capture device 1400, an image obtained by the camera may be monochrome or colored.

Illumination device 1500 is used to illuminate inspection object W in order to obtain an image which is easily to be inspected. As illumination device 1500, a fluorescent lamp or an LED may be used. Illumination device 1500 may be on at all times, otherwise, may stroboscopically illuminate the object in synchronization with a capturing timing of capture device 1400.

Figure 2:
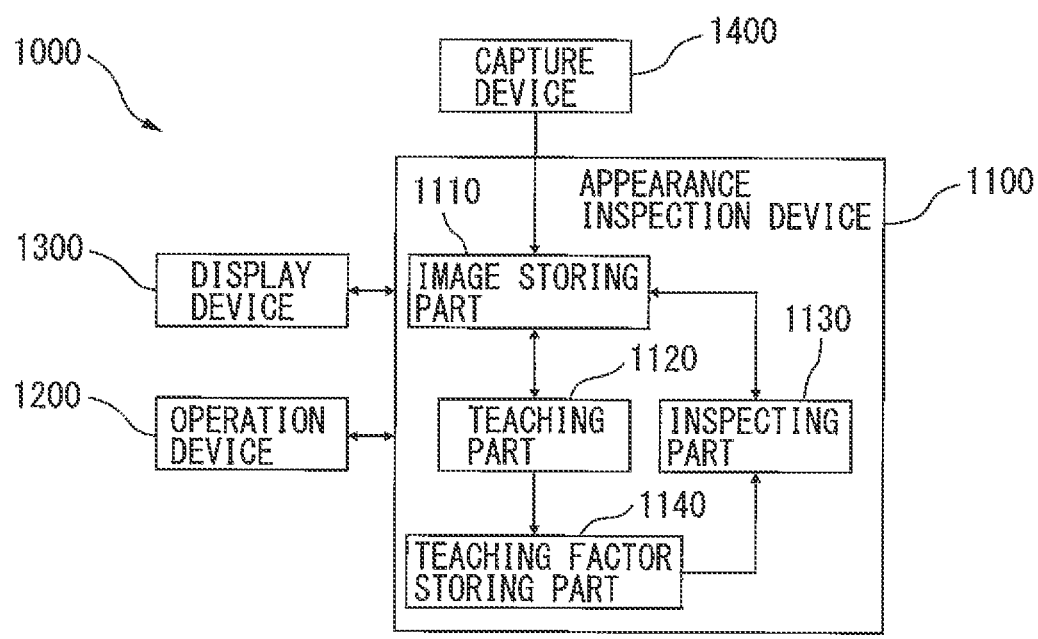
FIG. 2 is a functional block diagram of the system of FIG. 1.

FIG. 2 is a functional block diagram of system 1000. Appearance inspection device 1100 has an image storing part 1110, a teaching part 1120, an inspecting part 1130 and an inspection factor storing part 1140. Image storing part 1110 temporarily stores an image of an object captured by capture device 1400. Image storing part 1110 also stores an image of the object used in a teaching process of the inspection, and an image of the inspection object in an executing process of the inspection.

Teaching part 1120 obtains an image of the inspection object from image storing part 1110 in the teaching process of the inspection, and teaches the position of an inspection point, the position and the angle of an inspection region relative to the inspection point, the inspection factor and a judgment condition for the inspection, while displaying the image and the setting parameter on display device 1300 and changing the setting parameter if needed.

Teaching factor storing part 1140 stores the setting parameter which is set by teaching part 1120 and the teaching factor taught by teaching part 1120.

Inspecting part 1130 executes inspection based on the teaching factor stored in teaching factor storing part 1140, in the inspecting process. By virtue of appearance inspection device 1100 including such a configuration, the inspection can be executed in various ways, depending on the kind of the inspection object and/or the purpose of inspection.

Hereinafter, an inspection method using the appearance inspection device will be explained, with reference to five working examples.

WORKING EXAMPLE 1

Figure 3A:
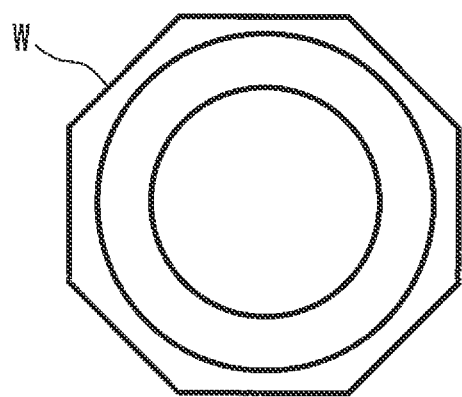
FIG. 3a shows an inspection object in a first working example.
Figure 3B:
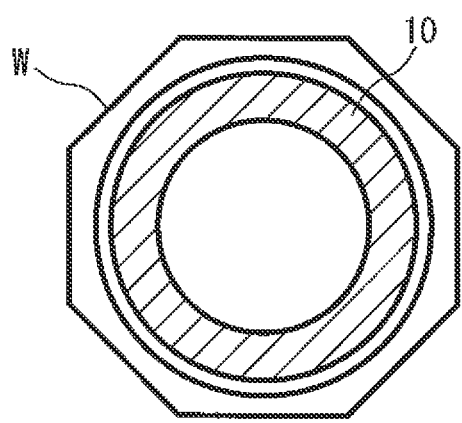
Figure 3C:
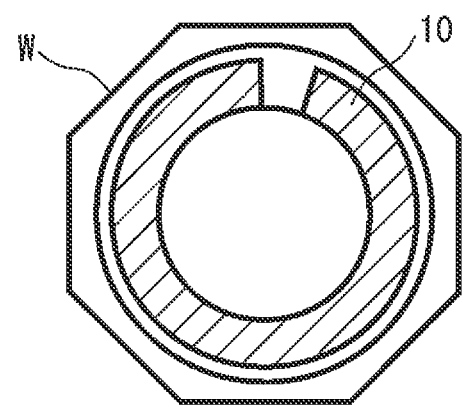

In a first working example (working example 1), a basic operation of the appearance inspection device is explained, wherein adhesive agent is annularly applied to a surface of inspection object W having a generally octagonal planar shape, and an appearance of inspection object W is inspected. FIG. 3*a* shows inspection object W before the adhesive agent is applied to the object, and FIG. 3*b* shows inspection object W to which adhesive agent 10 is appropriately applied. In the first working example, it is judged as to whether adhesive agent 10 is annularly applied to the inspection object in a seamless manner, by measuring the brightness of applied adhesive agent 10. FIG. 3*c* shows an inappropriate example, wherein applied adhesive agent has an incision. The first working example is intended to judge that the application state of inspection object W is "PASS" in the case of FIG. 3*b*, and is "FAIL" in the case of FIG. 3*c*.

Figure 4:
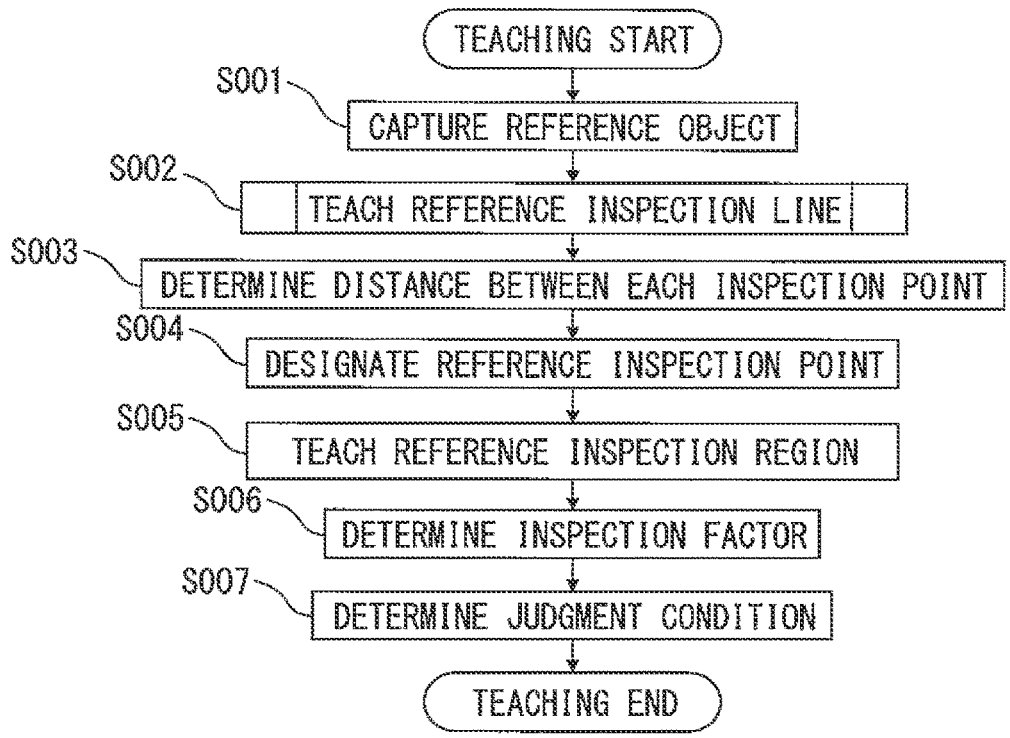
FIG. 4 is a flowchart explaining a procedure in a teaching process.
Figure 5:
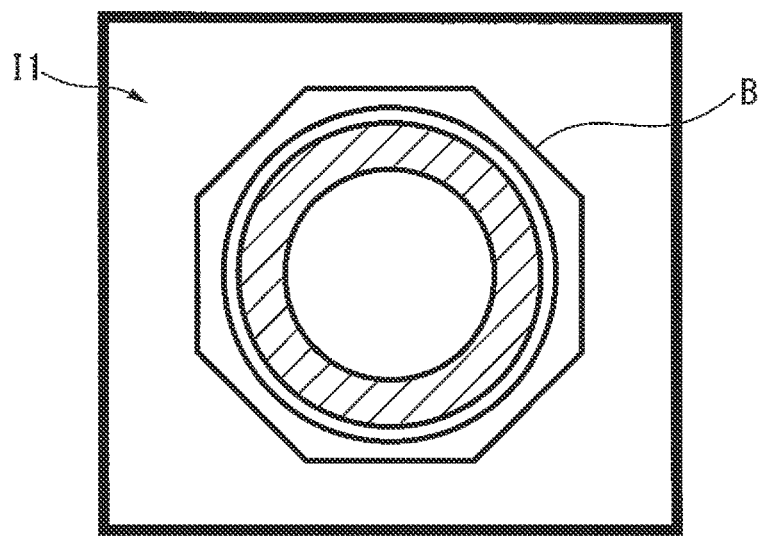
FIG. 5 shows an image of a reference inspection object.

Next, with reference to a flowchart in FIG. 4, the procedure of the teaching process executed by teaching part 1120 is explained. First, in step S001, a reference inspection object (hereinafter, also referred to as a reference object) B is located within a field of view of capture device 1400. In this regard, reference object B is an inspection object to which adhesive agent is appropriately applied in seamless manners. Then, reference object B is captured by capture device 1400 so as to obtain a first image or a reference object image I1 as shown in FIG. 5. Reference object image I1 is stored in image storing part 1110 and is displayed on display device 1300.

Next, in step S002, a reference inspection line 21 is taught so as to indicate a portion to be inspected. In the first working example, the reference inspection line is taught along with a center line of adhesive agent 10 (see FIG. 12 described below). Hereinafter, some examples of the teaching method for reference inspection line 21 are explained with reference to FIGS. 6 to 12.

Figure 6:
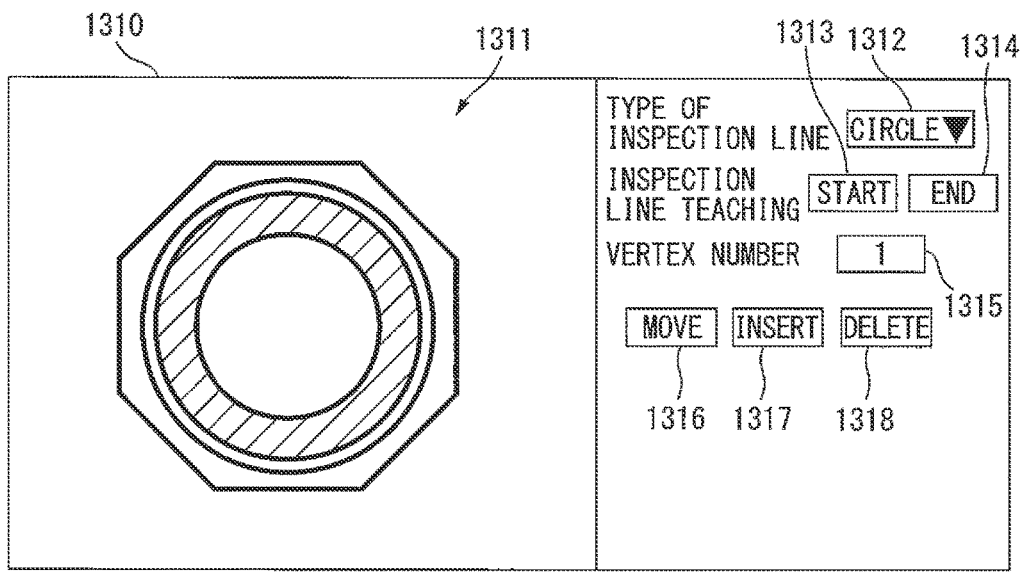
FIG. 6 shows a display example of a display device of the system of FIG. 1.

FIG. 6 shows an example of a display for teaching reference inspection line 21 displayed on display device 1300. In this case, reference inspection line 21 is taught by means of an inspection line setting display 1310 displayed on display device 1300 and user operation using operation device 1200. Inspection line setting display 1310 includes an image display section 1311 on which reference object image I1 is displayed, a drop-down box 1312 for selecting a line type of reference inspection line 21, a teaching start button 1313 for initiating the teaching of reference inspection line 21, a teaching end button 1314 for terminating the teaching of reference inspection line 21, an input box 1315 for adjusting reference inspection line 21, a move button 1316, an insert button 1317 and a delete button 1318.

Figure 7:
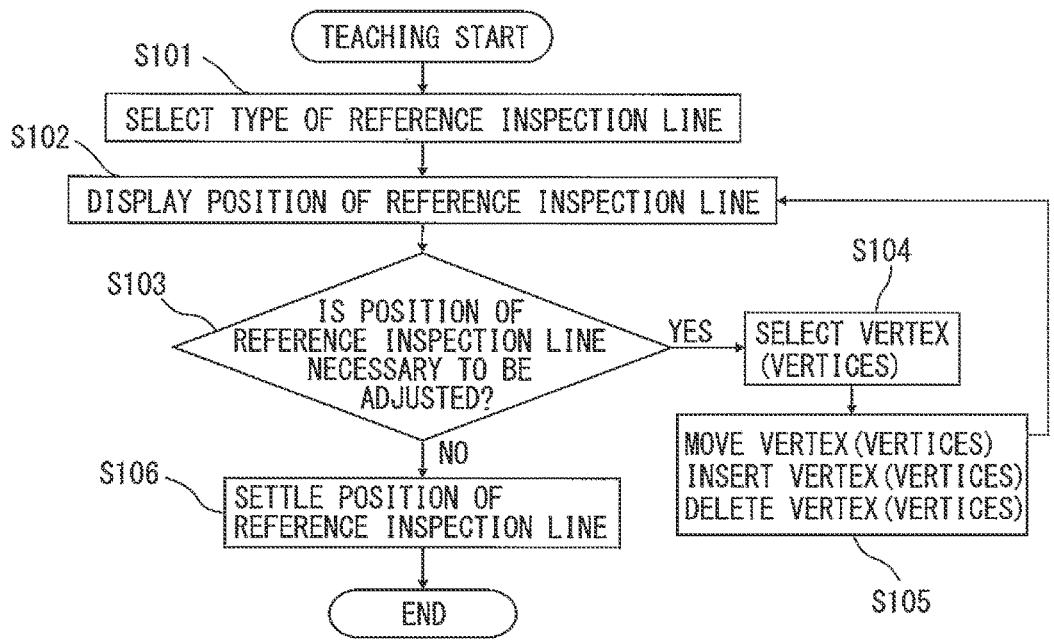
FIG. 7 is a flowchart explaining a teaching procedure for a reference inspection line in the teaching process.
Figure 8:
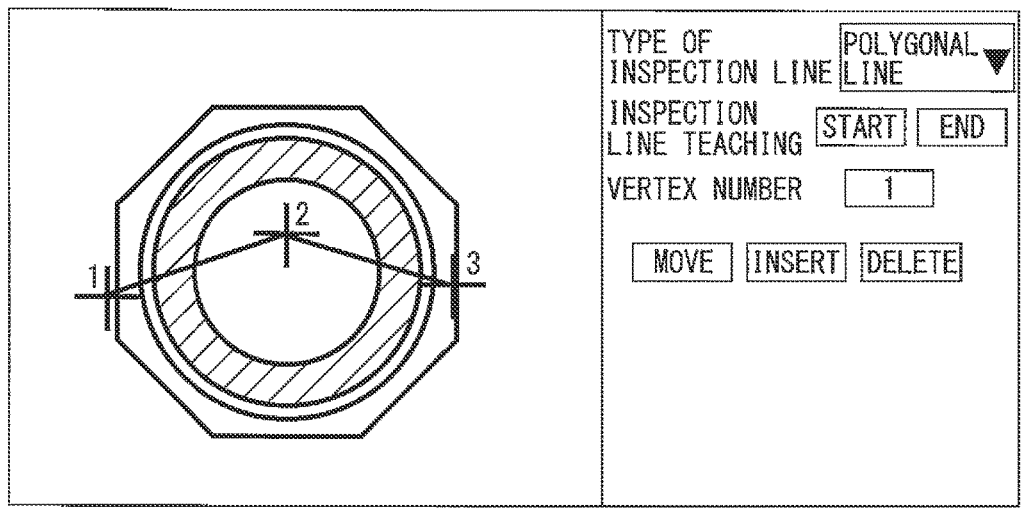
FIG. 8 shows an example wherein a polygonal line is taught as the reference inspection line.
Figure 9:
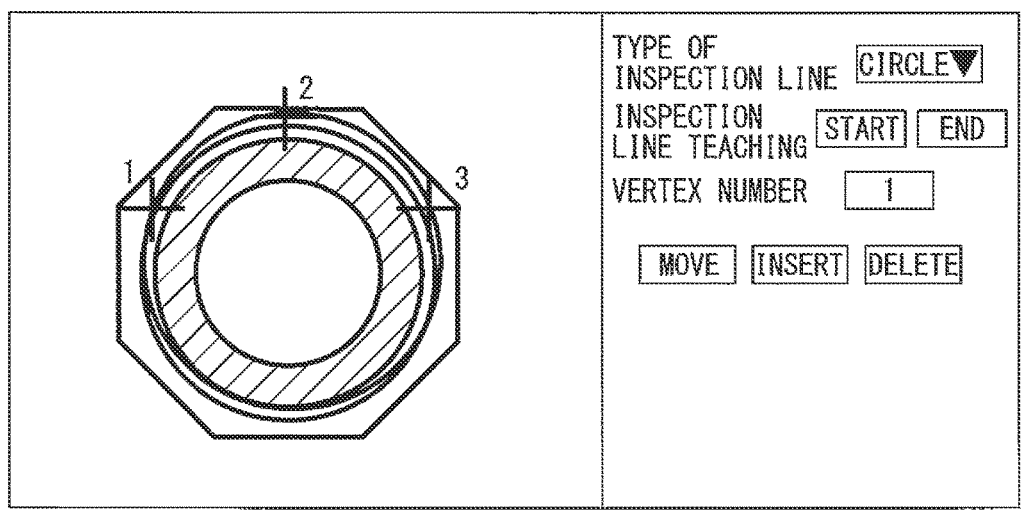
FIG. 9 shows an example wherein an arc is taught as the reference inspection line.
Figure 10:
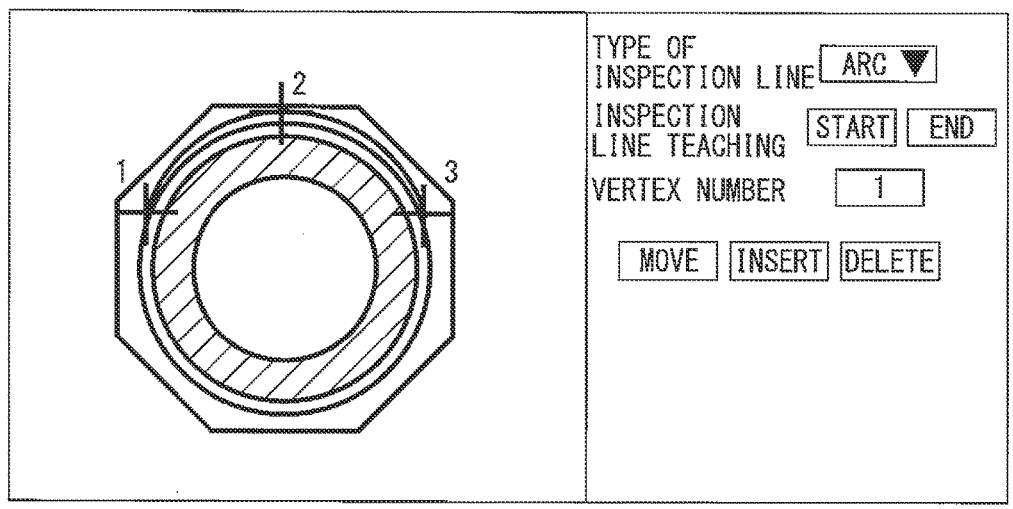
FIG. 10 shows an example wherein a circle is taught as the reference inspection line.
Figure 11:
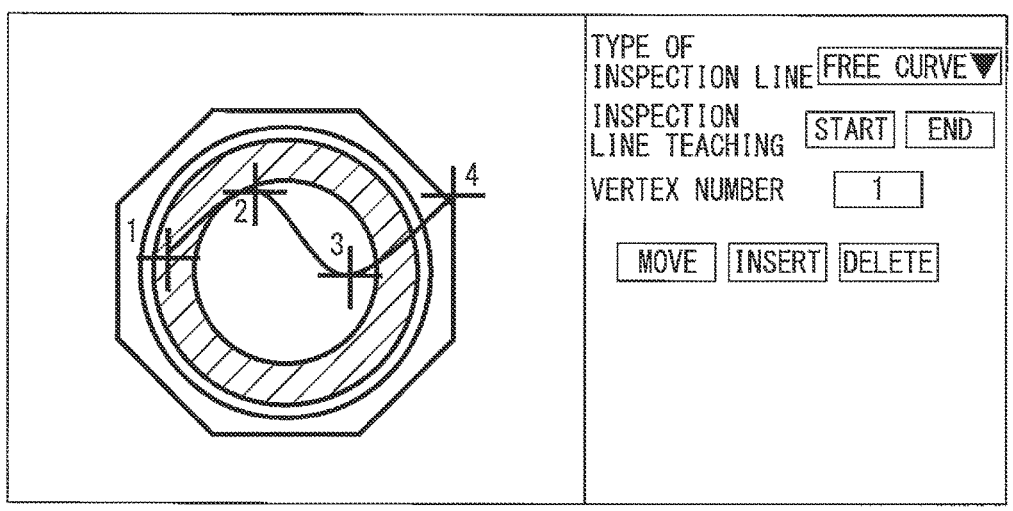
FIG. 11 shows an example wherein a free curve is taught as the reference inspection line.

Next, with reference to a flowchart of FIG. 7, the procedure for teaching reference inspection line 21 by user operation is explained. First, in step S101, a line type of reference inspection line 21 is selected by means of drop-down box 1312. In this case, one of a "polygonal line," a "circle," an "arc" and a "free line" can be selected, otherwise, a combination thereof may be used to teach reference inspection line 21.

Next, in step S102, teaching start button 1313 is pushed so as to initiate teaching of reference inspection line 21. A line having the line type selected in step S101 is overlapped with image I1 of reference object B displayed on image displaying section 1311. FIGS. 8 to 11 show examples wherein the "polygonal line," the "circle," the "arc" and the "free line" are selected as the line type of reference inspection line 21, respectively.

In this working example, reference inspection line 21 is constituted by a plurality of points or vertices. For example, when the "polygonal line" is selected, a polygonal line constituted by connecting each vertex corresponds to reference inspection line 21. Otherwise, when the "circle" is selected, a circle passing through three points corresponds to reference inspection line 21. By changing the positions of the vertices, the position and/or the shape of reference inspection line 21 can be adjusted. At this time point, indicated each vertices of reference inspection line 21 corresponds to an initial position, and the position and/or the shape of reference inspection line 21 is adjusted by changing the position of the vertex based on the procedure as described below. In this example, since adhesive agent 10 to be inspected is annularly formed, the "circle" is selected as the line type of the inspection line.

Next, in step S103, if the position and/or the shape of reference inspection line 21 should be adjusted, the procedure progresses to step S104. Otherwise, if the adjustment is not necessary, i.e., if reference inspection line 21 is already adjusted so as to be positioned along the center line of adhesive agent 10, the procedure progresses to step S106.

The position and the shape of the reference inspection line can be adjusted by arranging (i.e., adding, deleting or moving) the vertices. In this regard, the vertex (vertices) to be arranged is (are) selected in step S104. Among the vertices constituting reference inspection line 21, the vertex (vertices) to be arranged is (are) selected by using input box 1315.

In the next step S105, by pushing move button 1316, insert button 1317 or delete button 1318, the vertex (vertices) selected in step S104 is (are) moved, inserted or deleted. When the selected vertex (vertices) is (are) moved, inserted or deleted, the image displayed on image displaying section 1311 is updated. After the vertices constituting reference inspection line 21 are arranged necessary times so that reference inspection line 21 is adjusted so as to be positioned along the center line of adhesive agent 10, the procedure progresses to step S106.

Figure 12:
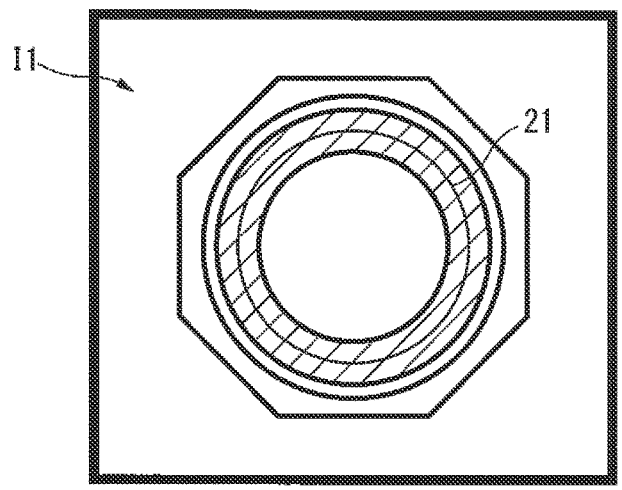
FIG. 12 shows an image of the reference inspection object wherein the reference inspection line is taught.

Finally, in step S106, by pushing teaching end button 1314, the teaching of reference inspection line 21 is terminated, and the position and the shape of reference inspection line 21 at this time point are stored in teaching factor storing part 1140. FIG. 12 shows an example of reference object image I1 displayed on display device 1300, after the teaching of the position of reference inspection line 21 is taught.

With reference to FIG. 4 again, after the teaching of reference inspection line 21 (S002) is completed, a distance between inspection points is taught in step S003. In this working example, the distance between the inspection points is set by a unit of pixel based on numerical entry using operation device 1200.

Figure 13A:
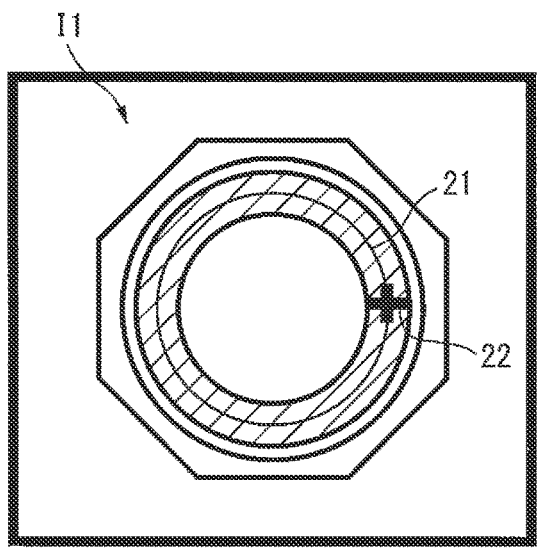
FIG. 13a shows an example wherein an inspection point is taught on the right side of the reference inspection line.
Figure 13B:
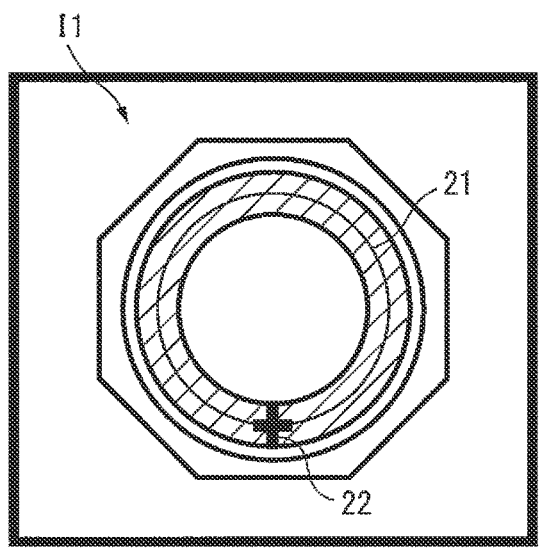
FIG. 13b shows an example wherein an inspection point is taught on the bottom side of the reference inspection line.

Next, in step S004, one point on reference inspection line 21 is designated as a reference inspection point 22. Some methods can be used to designate the position of reference inspection point 22. For example, as shown in FIGS. 13*a* and 13b, the position of reference inspection point 22 may be taught by: displaying a graphic of reference inspection line 21 on reference object image I1 displayed on display device 1200; displaying a cross-hair cursor on reference inspection line 21, which is capable of moving on reference inspection line 21 only; and moving the cross-hair cursor to a desired position on reference inspection line 21 by using operation device 1200. In the examples of FIG. 13a, reference inspection point 22 is taught so as to be positioned on the right side of circular reference inspection line 21, and in the example of FIG. 13b, reference inspection point 22 is taught so as to be positioned on the lower side of circular reference inspection line 21.

Figure 14:
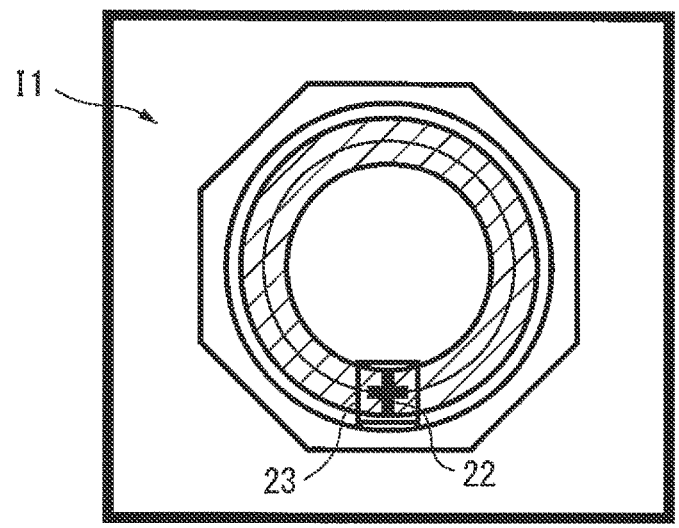
FIG. 14 shows an example wherein a reference inspection region is defined in relation to the reference inspection point.

Next, in step S005, a reference inspection region 23 is taught. Although there is no particular limitation regarding the shape of the reference inspection region, the shape of the region is rectangular in this working example, as shown in FIG. 14. In this case, the position and size can be determined by parameters such as the center position, a rotation angle, and the lengths of long and short sides thereof, etc. Graphics of reference inspection line 21 and reference inspection point 23 are displayed on reference object image I1 displayed on display device 1300, and a movable and rotatable rectangle is displayed on reference object image I1. The position and size of reference inspection region 23 are adjusted by moving the rectangle to a desired position and by rotating the rectangular cursor by a desired angle by means of operation device 1200. The adjusted position and size of reference inspection region 23 are stored in teaching factor storing part 1140, as well as the position of reference inspection point 22 designated in step S004. By virtue of this, as shown in FIG. 14, reference object image I1, with which reference inspection line 21, reference inspection point 22 and reference inspection region 23 are overlapped, is displayed on display device 1300.

Next, in step S006, an inspection factor is determined. In this working example, an average value of brightness of an image within a designated inspection region is measured. The determined inspection factor is stored in teaching factor storing part 1140.

Finally, in step S007, a judgment condition is determined. In this working example, a portion to which the adhesive agent is not applied is displayed on the image as a white portion, and a portion to which the adhesive agent is applied is displayed on the image as a black portion. Therefore, a judgment condition, wherein it is judged as "PASS" when an average value of brightness in the measured inspection region is lower than a specified brightness, while it is judged as "FAIL"

when the average value of brightness is higher than the specified brightness, is determined to be used. The determined judgment condition is stored in teaching factor storing part 1140.

Figure 15:
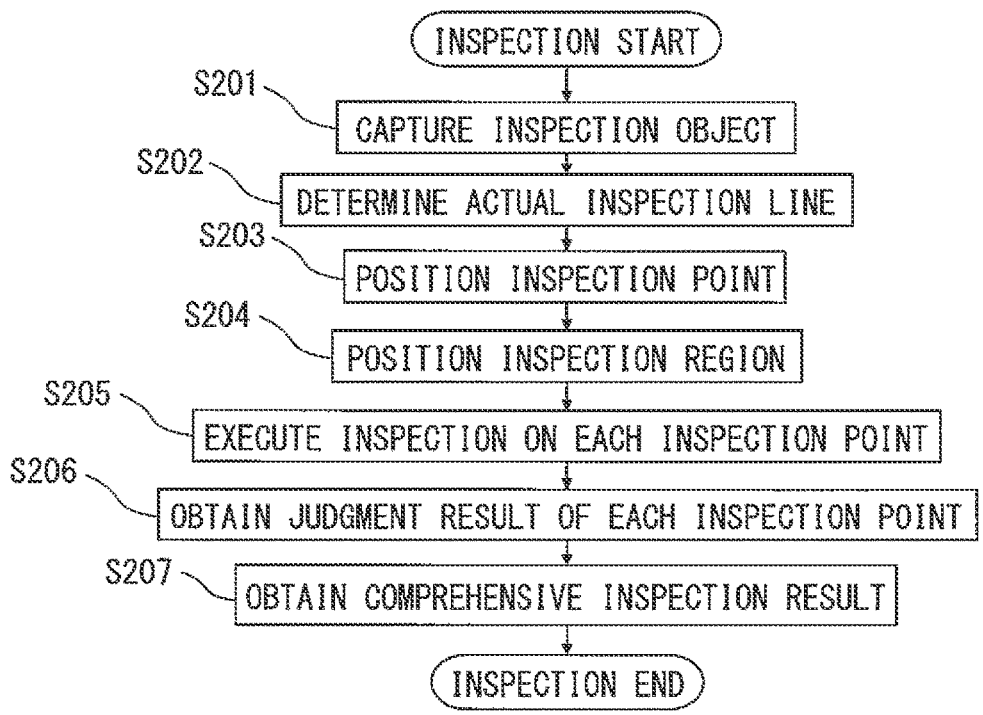
FIG. 15 is a flowchart explaining a procedure in an inspection process.
Figure 16:
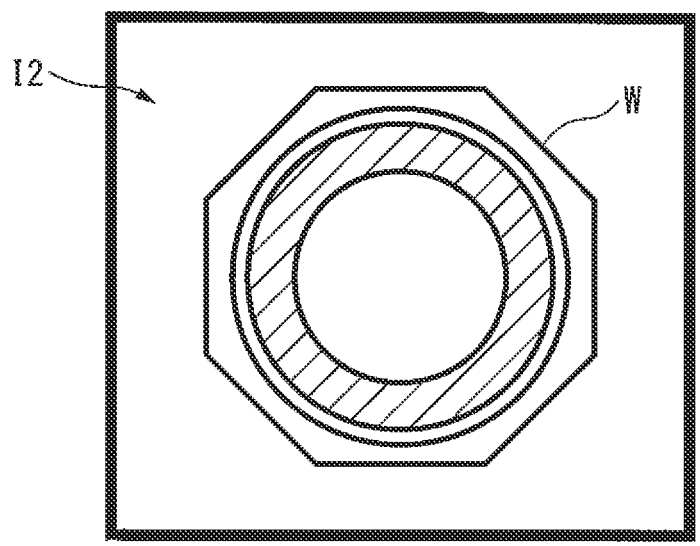
FIG. 16 shows an image of the inspection object in the first working example.

Next, with reference to a flowchart of FIG. 15, the procedure of the inspection process executed by inspecting part 1130 is explained. First, in step S201, inspection object W is located within the field of view of capture device 1400, and is captured by capture device 1400 so as to obtain a second image or an inspection object image I2 as shown in FIG. 16. Inspection object image I2 is stored in image storing part 1110.

Figure 17:
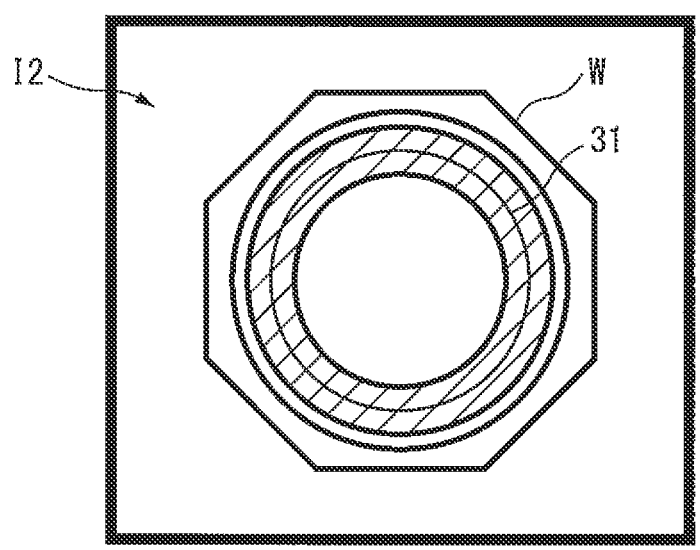
FIG. 17 shows an image of the inspection object wherein an actual inspection line is defined.

Next, in step S202, the teaching information of reference inspection line 21 is obtained as an actual inspection line 31 from teaching factor storing part 1140, and actual inspection line 31 is overlapped with inspection object image I2. Concretely, as shown in FIG. 17, display device 1300 displays an image wherein inspection object image I2 and actual inspection line 31 are overlapped with each other.

Next, in step S203, inspection points P1 to Pn are located on actual inspection line 31, wherein the character "n" is the number of the inspection points. In this working example, the inspection points are located at regular intervals on actual inspection line 31, based on an inspection point distance stored in teaching factor storing part 1140. The inspection point number n is calculated by dividing a total length of actual inspection line 31 by the inspection point distance stored in teaching factor storing part 1140. In the illustrated example, the number n is eight.

Figure 18:
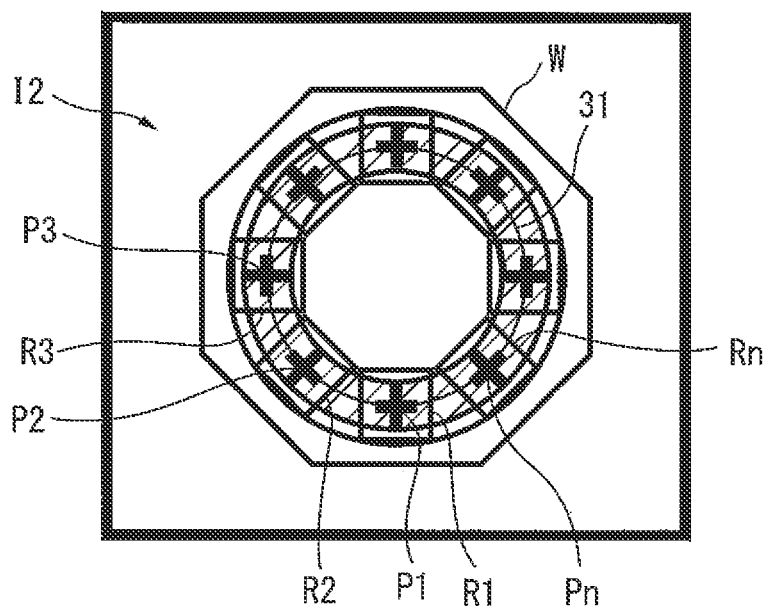
FIG. 18 shows an example wherein an inspection point and an inspection region are defined on the inspection object.

Next, in step S204, information of reference inspection point 22 and reference inspection 23 is obtained from teaching factor storing part 1140, and inspection regions R1 to Rn are arranged in relation to respective inspection points P1 to Pn so that a positional relationship between the inspection point and the inspection region is the same as a positional relationship between reference inspection point 22 and reference inspection region 23. As a result, as shown in FIG. 18, display device 1300 displays an image wherein inspection object image I2, actual inspection line 31, inspection points P1 to Pn, and inspection regions R1 to Rn are overlapped with each other.

Next, in step S205, average values of brightness of images within respective inspection regions R1 to Rn are measured, based on the inspection factor stored in teaching factor storing part 1140.

Next, in step S206, judgment results (PASS or NG) in inspection points P1 to Pn are determined and obtained, in relation to inspection regions R1 to Rn, respectively, based on the measured average value of brightness of the image and the judgment condition stored in teaching factor storing part 1140. In this regard, display device 1300 may display an image wherein inspection object image I2, actual inspection line 31, inspection points P1 to Pn, inspection regions R1 to Rn, and the results of judgment in inspection points P1 to Pn (PASS or NG) are overlapped with each other.

Finally, in step S207, considering all of the results of judgment of inspection points P1 to Pn, an inspection result of the entire adhesive agent is determined and obtained. In an exemplified method therefor, the number of the inspection points judged as "FAIL" is counted, and the comprehensive judgment is determined as "FAIL" if any of the inspection points is judged as "FAIL." In this regard, display device 1300 may display an image wherein inspection object image I2, actual inspection line 31, inspection points P1 to Pn, inspection regions R1 to Rn, the results of judgment in inspection points P1 to Pn, and the result of the comprehensive judgment are overlapped with each other.

Figure 19:
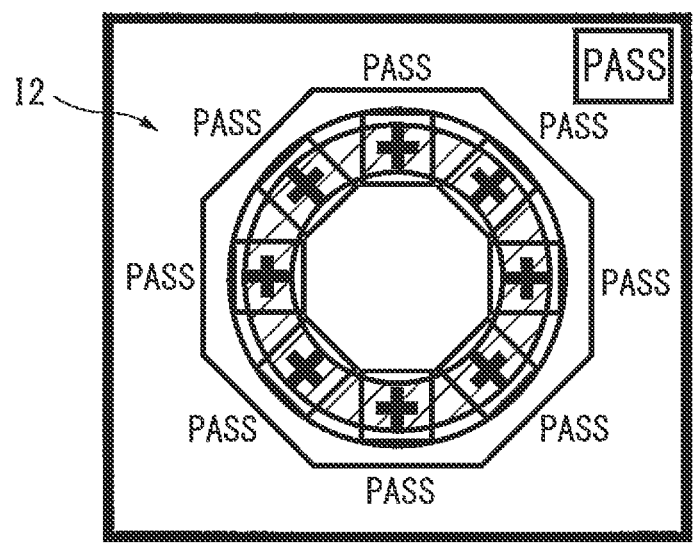
FIG. 19 shows an example wherein a comprehensive judgment is "PASS" in the first working example.
Figure 20:
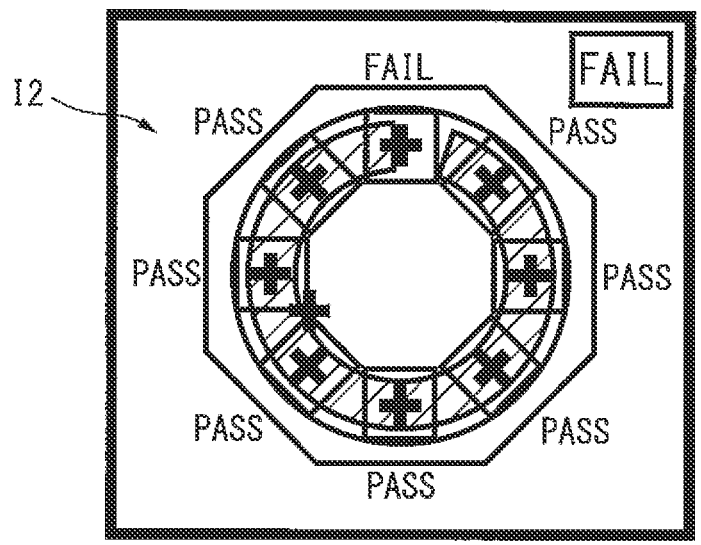
FIG. 20 shows an example wherein a comprehensive judgment is "FAIL" in the first working example.

FIGS. 19 and 20 exemplify the results of the comprehensive judgment in step S207. In detail, FIG. 19 shows an image displayed on display device 1300 wherein all of the inspection points are judged as "PASS" and the comprehensive judgment is also "PASS," i.e., the adhesive agent is appropriately applied to inspection object W in a seamless manner. On the other hand, FIG. 20 shows an image displayed on display device 1300 wherein the comprehensive judgment is "FAIL" since one inspection point is judged as "FAIL," i.e., the adhesive agent applied to inspection object W has an incision.

WORKING EXAMPLE 2

In the first working example, it is necessary that inspection object W be positioned by means of a positioning device so that inspection object W is located at the same position as reference object B. Otherwise, in a captured image, inspection object W may be located at a position different from a position of reference object B, whereby a correct portion of the object may not be inspected. Therefore, in a second working example (working example 2), a procedure, wherein inspection object W is not positioned in place, will be explained.

Figure 21:
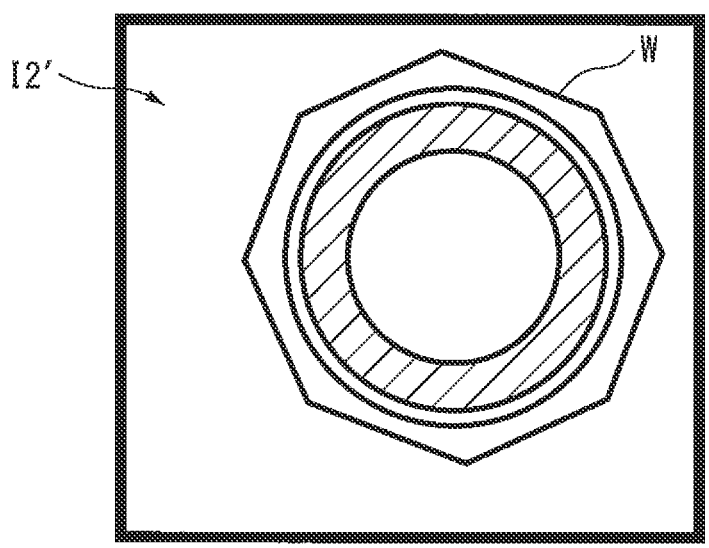
FIG. 21 shows an image of an inspection object in a second working example.

First, an inspection object image I2' as shown in FIG. 21 is considered, wherein inspection object W is not positioned in place. Concretely, in comparison to inspection object image I2 as shown in FIG. 16, inspection object W in image I2' is slightly moved to a right-upper side and is rotated by some degrees.

The procedure in working example 2 is different from working example 1 in the following matter, and the other matters of working example 2 may be the same as working example 1.

In the teaching process, after obtaining reference object image I1 in step S001, a step for identifying the position of reference object B displayed on image I1 is added. For example, by a template matching approach using a conventional normalized correlation method, a profile of the object (in the illustrated example, an octagonal shape) may be detected so as to identify the position of reference object B in reference inspection image I1. The identified position of reference object B is stored in teaching factor storing part 1140.

Further, in the inspection process, after capturing inspection object W so as to obtain inspection object image I2' in step S201, a step for identifying the position of inspection object W within image I2' is added. It is preferable that the identification of the position of inspection object W be executed in the same way as the identification of the position of reference object B in the teaching process. In addition, in step S202, actual inspection line 31 is positioned so that a positional relationship between actual inspection line 31 and identified inspection object W is the same as a positional relationship between reference inspection line 21 and reference inspection object B stored in teaching factor storing part 1140.

Figure 22:
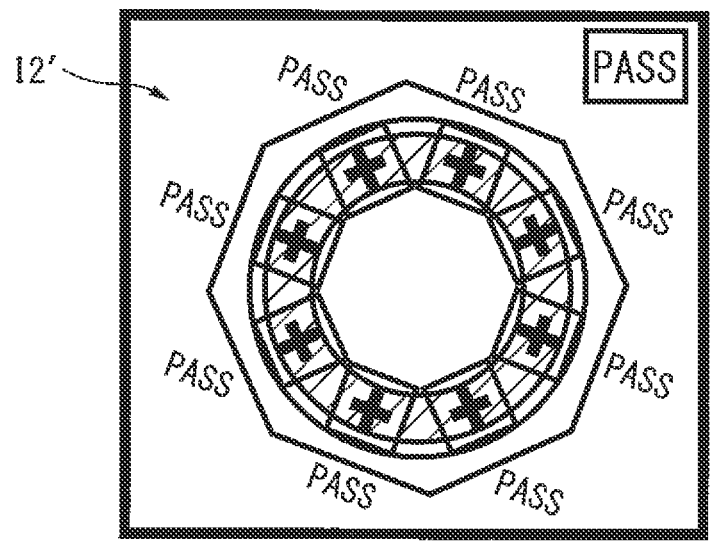
FIG. 22 shows an example wherein a comprehensive judgment is "PASS" in the second working example.
Figure 23:
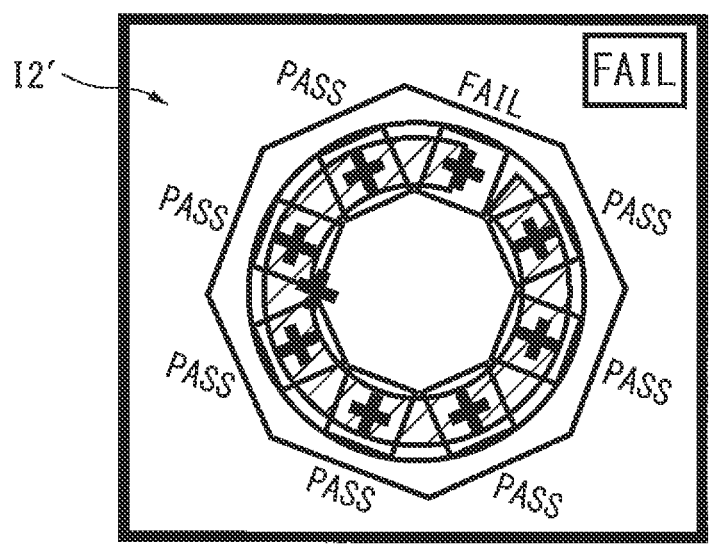
FIG. 23 shows an example wherein a comprehensive judgment is "FAIL" in the second working example.

By virtue of the above procedure, even when inspection object W is not positioned in place, actual inspection line 31 properly adapted to adhesive agent 10 applied to inspection object W can be determined and displayed. FIGS. 22 and 23 exemplify inspection results regarding inspection object image I2'. Concretely, FIG. 22 shows the result corresponding to FIG. 19, and FIG. 23 shows the result corresponding to FIG. 20 (i.e., FIG. 22 is "PASS," and FIG. 23 is "FAIL").

WORKING EXAMPLE 3

Figure 24:
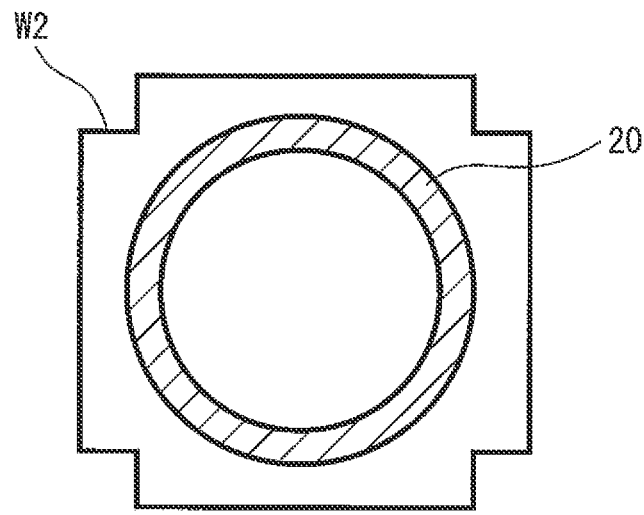
FIG. 24 shows an image of an inspection object in a third working example.

In a third working example (working example 3), a case wherein a plurality of inspection regions are defined in relation to each inspection point is explained. For example, as shown in FIG. 24, an O-ring 20 is attached to a predetermined portion of inspection object W2, and the brightness is measured in relation to both inside and outside regions of O-ring 20. By comparing the brightness between the inside and outside regions, it can be inspected or judged as to whether O-ring 20 is deviated from the predetermined portion.

The procedure in working example 3 is different from working example 1 in the following matter, and the other matters of working example 3 may be the same as working example 1.

Figure 25:
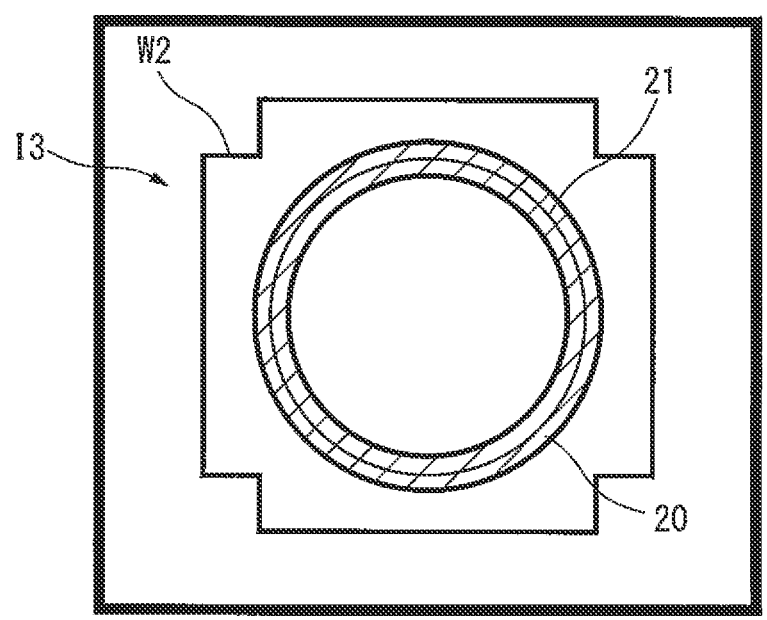
FIG. 25 shows an image of a reference inspection object wherein a reference inspection line is taught.
Figure 26:
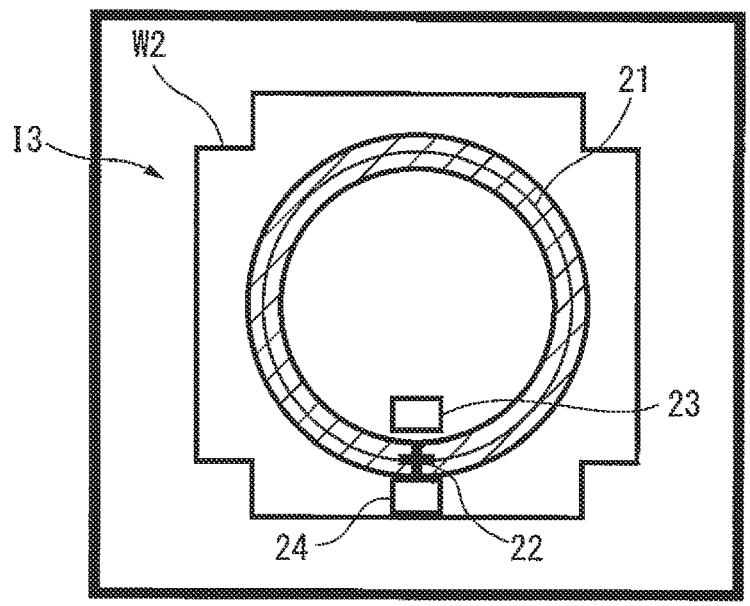
FIG. 26 shows an example wherein a reference inspection point and a reference inspection region are defined in the image of FIG. 25.

In step S002 of the teaching process, as shown in FIG. 25, reference inspection line 21 is taught along the center line of O-ring 20 displayed on inspection object image I3. Next, when the reference inspection region is taught in step S005, two reference inspection regions 23 and 24 are taught so that reference inspection point 22 is positioned between the two regions which are respectively positioned the inside and outside of O-ring 20, as shown in FIG. 26.

Further, the inspection factor to be set in step S006 is determined as a difference between an average value of the brightness in inspection region 23 and an average value of the brightness in inspection region 24. Then, as the judgment condition to be set in step S007, it is judged as "PASS" when the difference between the average values of the measured brightness in the two inspection regions is equal to or lower than a predetermined threshold. Otherwise, it is judged as "FAIL" when the difference exceeds the predetermined threshold.

Figure 27:
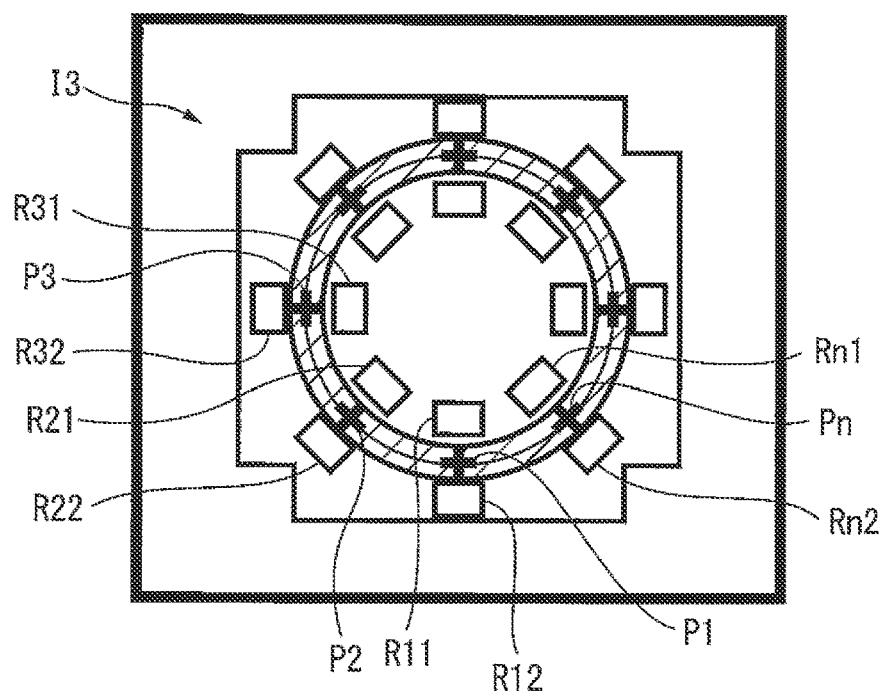
FIG. 27 shows an example wherein an actual inspection line, an inspection point and an inspection region are defined in the image of the inspection object.

In step S204 of the inspection process, as shown in FIG. 27, in relation to each of inspection points P1 to Pn located at predetermined intervals, inspection regions R11 and R12, R21 and R22, . . . , Rn1 and Rn2 are positioned and displayed, respectively, so that each inspection point is positioned between the corresponding inspection regions positioned the inside and outside of O-ring 20. In the third working example, by comparing the brightness of the two inspection regions sandwiching each inspection point, the brightness of the inner and outer regions of O-ring 20 can be compared to each other.

Figure 28:
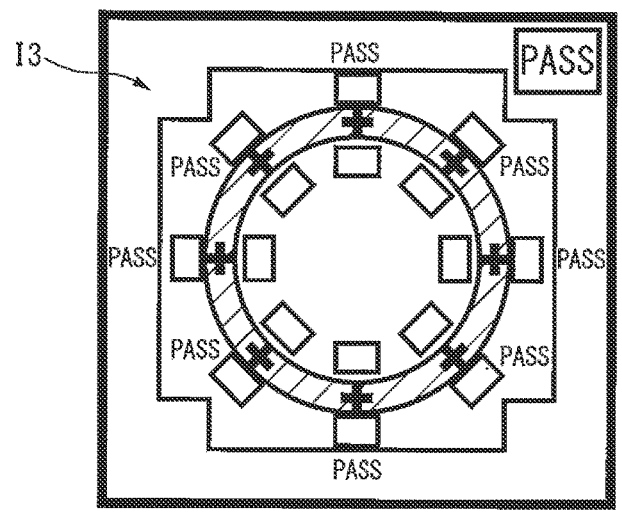
FIG. 28 shows an example wherein a comprehensive judgment is "PASS" in the third working example.
Figure 29A:
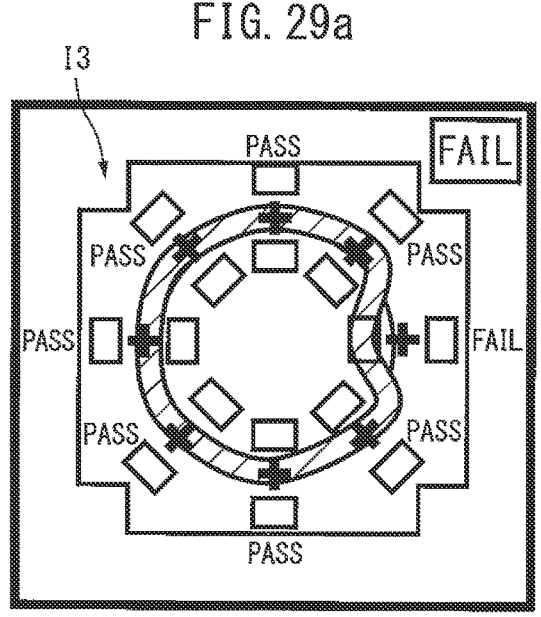
FIG. 29a shows an example wherein a comprehensive judgment is "FAIL" in the third working example, since a portion of an O-ring is deviated.
Figure 29B:
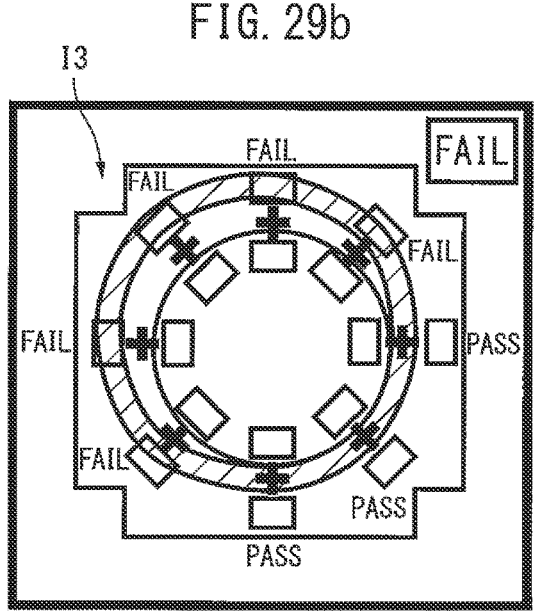
FIG. 29b shows an example wherein a comprehensive judgment is "FAIL" in the third working example, since a large portion of an O-ring is deviated.

FIG. 28 shows an example of an image displayed on display device 1300, wherein all of the inspection points are judged as "PASS" and the comprehensive judgment is also "PASS." In other words, FIG. 28 shows the inspection result when the O-ring is appropriately attached to inspection object W2. On the other hand, FIGS. 29*a* and 29*b* show examples of images displayed on display device 1300, wherein at least one of the inspection points is judged as "FAIL." In detail, FIG. 29*a* shows an example wherein the comprehensive judgment is "FAIL" since one inspection point is judged as "FAIL," i.e., the O-ring is partially deviated from the predetermined portion. On the other hand, FIG. 29*b* shows an example wherein the comprehensive judgment is "FAIL" since a plurality of (five in the drawing) inspection points are judged as "FAIL," i.e., the O-ring is deviated from the predetermined portion over a wide region.

In addition, the number of inspection regions positioned regarding one inspection point is not limited to two, i.e., three or more inspection regions may be positioned regarding one inspection point depending on contents of the inspection.

WORKING EXAMPLE 4

Figure 30:
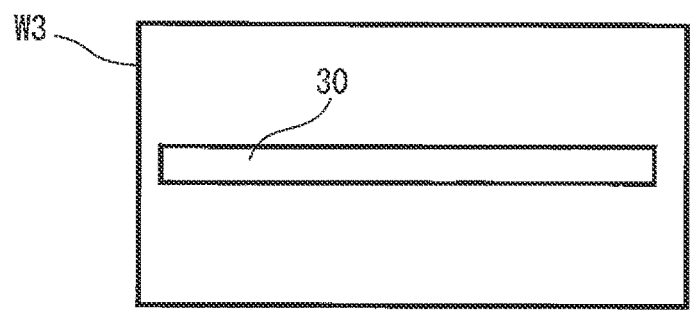
FIG. 30 shows an image of an inspection object in a fourth working example.

In a fourth working example (working example 4), a case wherein a width of the inspection object is inspected in relation to each inspection point is explained. For example, as shown in FIG. 30, regarding inspection object W3 having a surface to which sealing agent 30 is applied, the width of sealing agent 30 is measured, and then it is judged as to whether sealing agent 30 is applied to the object in a predetermined width.

The procedure in working example 4 is different from working example 1 in the following matter, and the other matters of working example 4 may be the same as working example 1.

Figure 31:
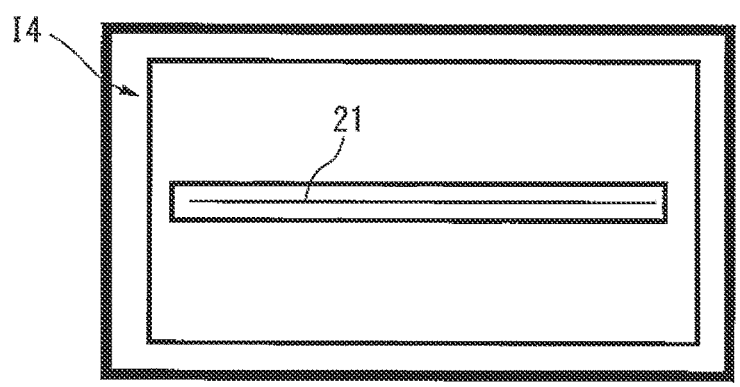
FIG. 31 shows an image of a reference inspection object wherein a reference inspection line is taught.
Figure 32:
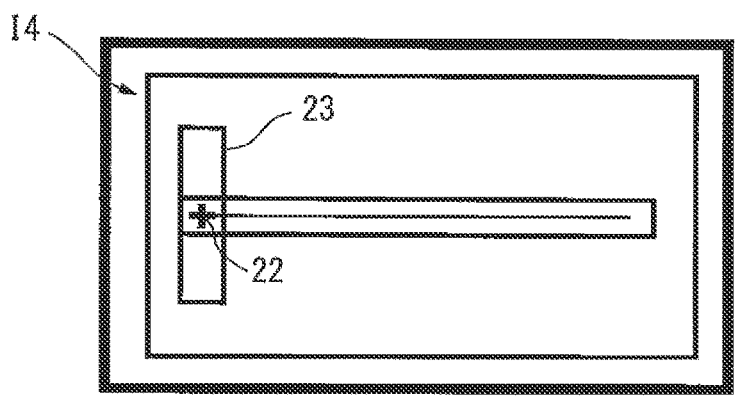
FIG. 32 shows an example wherein a reference inspection point and a reference inspection region are defined in the image of FIG. 31.

In step S002 of the teaching process, as shown in FIG. 31, reference inspection line 21 is taught along the center line of sealing agent 30 displayed on inspection object image I4. Next, when the reference inspection region is taught in step S005, reference inspection region 23 having a rectangular shape, the center of which corresponds to designated inspection point 22, is positioned, as shown in FIG. 32. The dimension of reference inspection region 23 is larger than sealing agent 30, at least regarding the width direction of sealing agent 30, i.e., reference inspection region 23 is formed so as to protrude from sealing agent 30 in the width direction thereof.

Further, the inspection factor to be set in step S006 is determined as the width of the sealing agent in each inspection region. Then, as the judgment condition to be set in step S007, it is judged as "PASS" when the measured width of the sealing agent in the inspection region is within a predetermined range. Otherwise, it is judged as "FAIL" when the measured width is out of the predetermined range.

Figure 33:
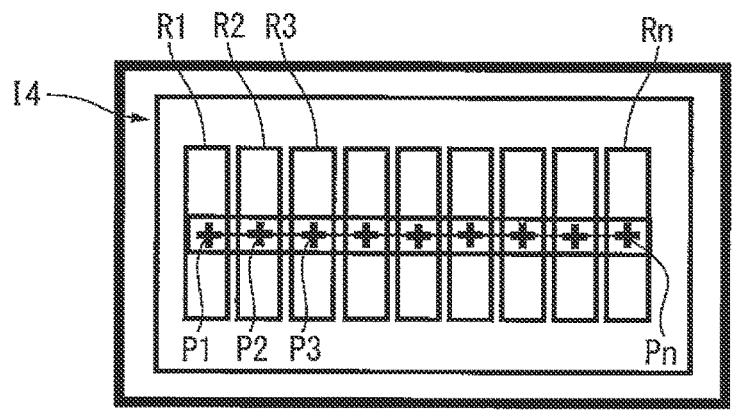
FIG. 33 shows an example wherein an actual inspection line, an inspection point and an inspection region are defined in the image of the inspection object.

In step S204 of the inspection process, as shown in FIG. 33, in relation to each of inspection points P1 to Pn located at predetermined intervals, inspection regions R1 to Rn are positioned and displayed, respectively. In the fourth working example, by inspecting the width of sealing agent 30 in relation to each inspection point, the width of the sealing agent can be inspected over the entire length thereof.

Figure 34:
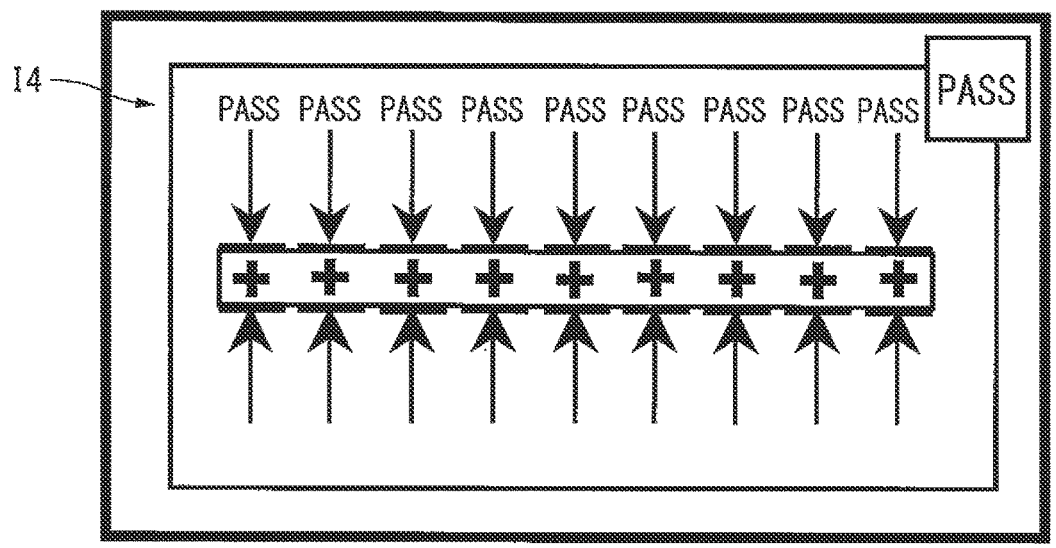
FIG. 34 shows an example wherein a comprehensive judgment is "PASS" in the fourth working example.
Figure 35:
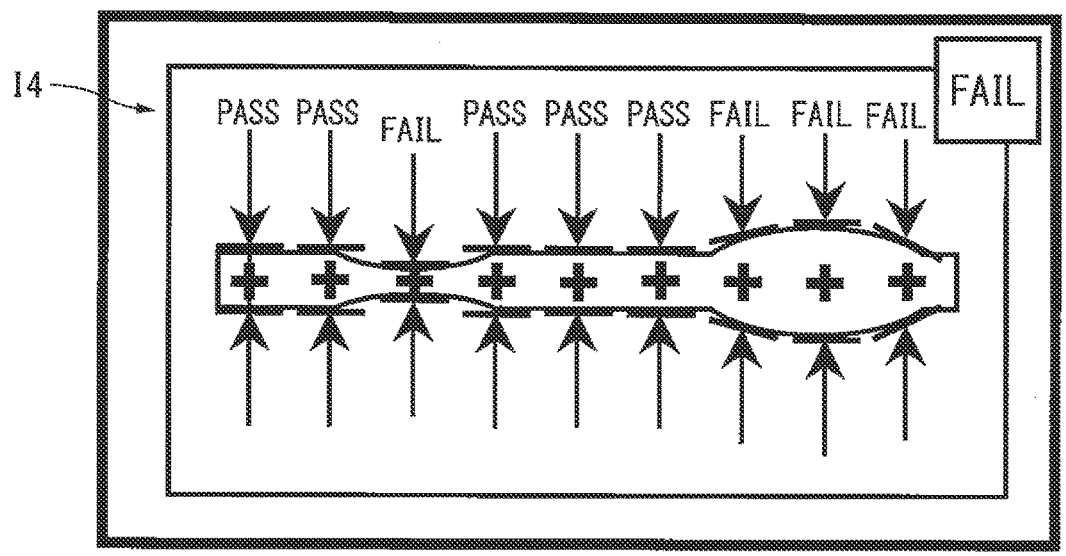
FIG. 35 shows an example wherein a comprehensive judgment is "FAIL" in the fourth working example.

FIG. 34 shows an example of an image displayed on display device 1300, wherein all of the inspection points are judged as "PASS" and the comprehensive judgment is also "PASS." In other words, FIG. 34 shows the inspection result when sealing agent 30 is appropriately applied to inspection object W3 in a predetermined width and in a seamless manner. On the other hand, FIG. 35 shows an example of an image displayed on display device 1300, wherein at least one of the inspection points is judged as "FAIL." In FIG. 35, in relation to some inspection points, the width of the sealing agent applied to inspection object W3 is smaller or larger than a predetermined threshold. Therefore, inspection results of the inspection points are judged as "FAIL," and the comprehensive judgment is also "FAIL" in the example of FIG. 35.

WORKING EXAMPLE 5

Figure 36:
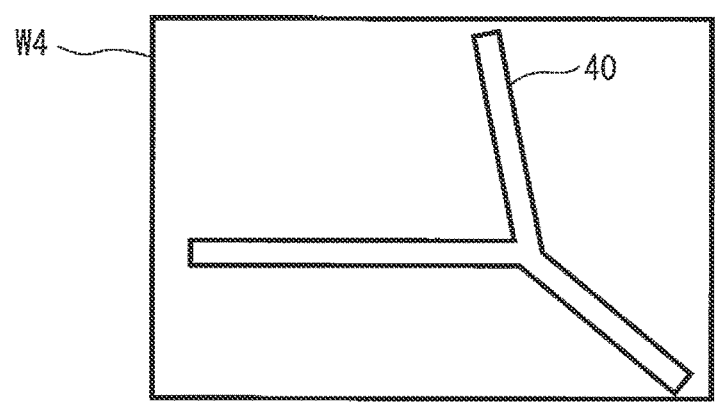
FIG. 36 shows an image of an inspection object in a fifth working example.

In a fifth working example (working example 5) as described below, it is intended to simultaneously execute two or more kinds of inspections. In the fifth working example, the third and fourth working examples are combined, so that the brightness and the width are simultaneously inspected in relation to each inspection point. Further, in the fifth working example, a portion to be inspected has a branch point. Concretely, as shown in FIG. 36, sealing agent 40 is applied to inspection object W4 so that sealing agent 40 has a bifurcated portion (or a Y-shape). Then, the brightness and the width of sealing agent 40 are measured, and it is judged as to whether sealing agent 40 is applied to a predetermined position of the object in a predetermined width.

The procedure in working example 5 is different from working example 1 in the following matter, and the other matters of working example 5 may be the same as working example 1.

Figure 37:
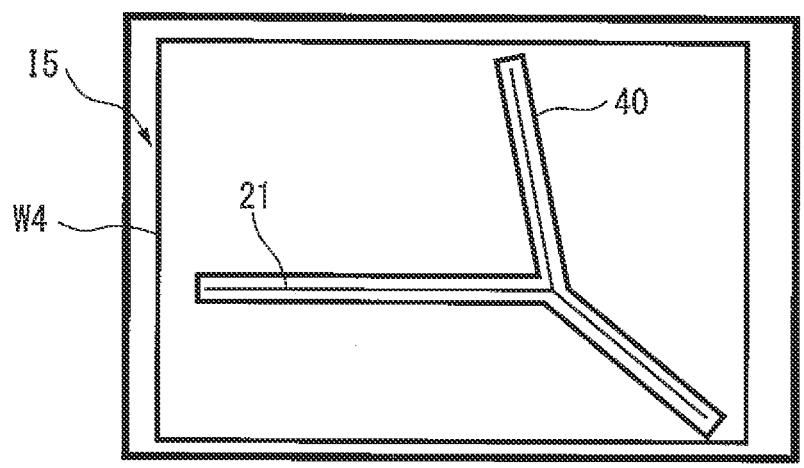
FIG. 37 shows an image of a reference inspection object wherein a reference inspection line is taught.

In step S002 of the teaching process, as shown in FIG. 37, reference inspection line 21 is taught along the center line of sealing agent 40 displayed on inspection object image I5 . In this regard, two polygonal lines are used to teach reference inspection line 21.

Figure 38:
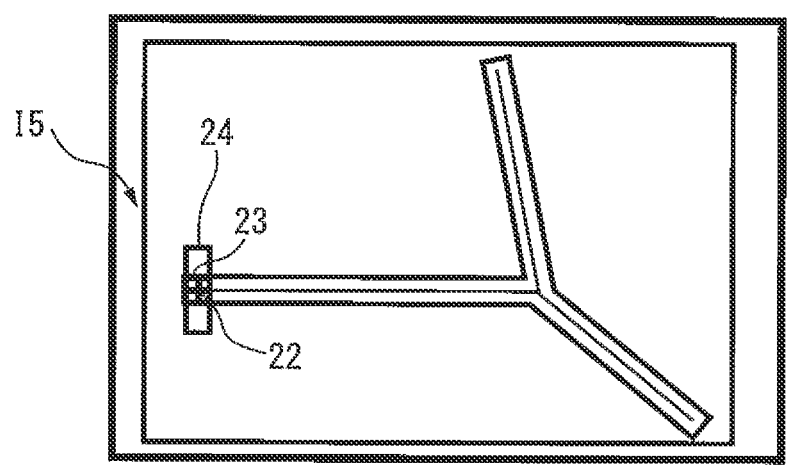
FIG. 38 shows an example wherein a reference inspection point and a reference inspection region are defined in the image of FIG. 37.

Next, in step S005, reference inspection regions 23 and 24 are taught in relation to inspection point 22, as shown in FIG. 38. Reference inspection region 23 is a region for measuring the brightness of the portion to which the sealing agent is applied, and is configured as a square or rectangular shape, the center of which corresponds to reference inspection point 22, so that region 23 does not protrude from sealing agent 40. On the other hand, Reference inspection region 24 is a region for measuring the width of the applied sealing agent, and is configured as a rectangular shape, the center of which corresponds to reference inspection point 22, so that region 24 widely protrudes from sealing agent 40 in the width direction thereof, as shown in FIG. 38.

The inspection factor to be set in step S006 is determined as an average value of brightness within the inspection region in relation to reference inspection region 23 where the brightness is inspected, and as the width of the sealing agent in relation to reference inspection region 24 where the width is inspected. Then, as the judgment condition to be set in step S007, it is judged as "PASS" when the average value of brightness of reference inspection region 23 is equal to or lower than a predetermined threshold and when the measured width of the sealing agent in reference inspection region 24 is within a predetermined range. Otherwise, it is judged as "FAIL" when at least one of the above two conditions is not satisfied.

Figure 39:
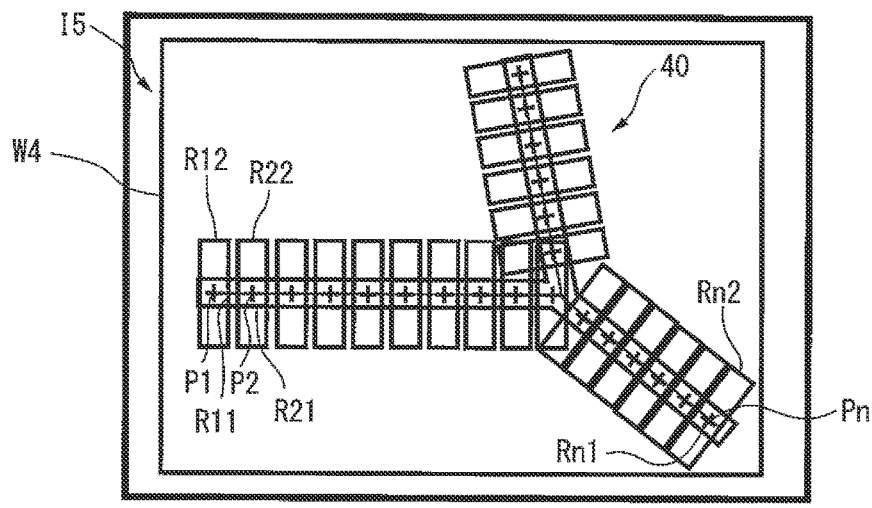
FIG. 39 shows an example wherein an actual inspection line, an inspection point and an inspection region are defined in the image of the inspection object.

In step S204 of the inspection process, as shown in FIG. 39, in relation to each of inspection points P1 to Pn located at predetermined intervals, inspection regions R11 and R12, R21 and R22, . . . , Rn1 and Rn2 are positioned and displayed, respectively. In the fifth working example, in relation to each inspection point, the rightness and the width of sealing agent 40 can be simultaneously inspected over the entire length thereof.

Figure 40:
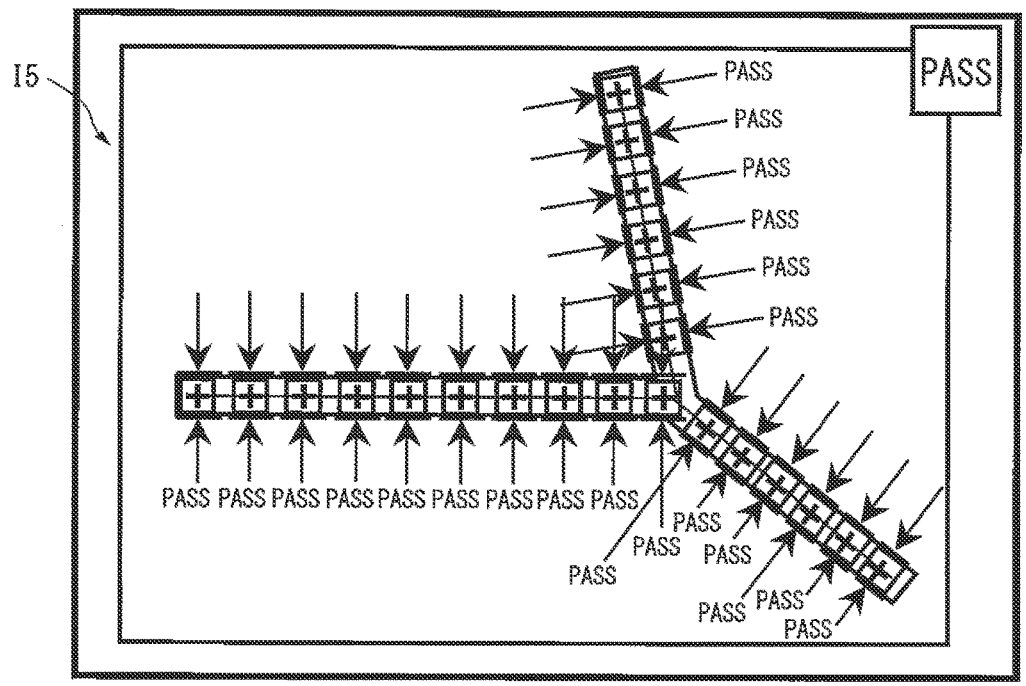
FIG. 40 shows an example wherein a comprehensive judgment is "PASS" in the fifth working example.
Figure 41A:
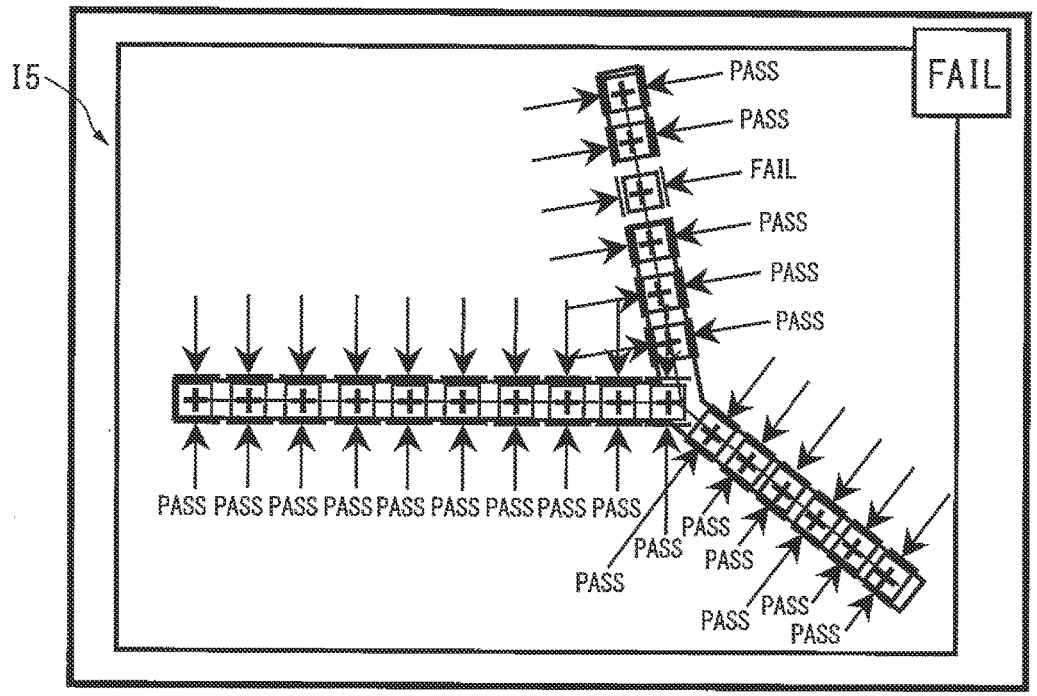
FIG. 41a shows an example wherein a comprehensive judgment is "FAIL" in the fifth working example, since a portion of sealing agent is broken.
Figure 41B:
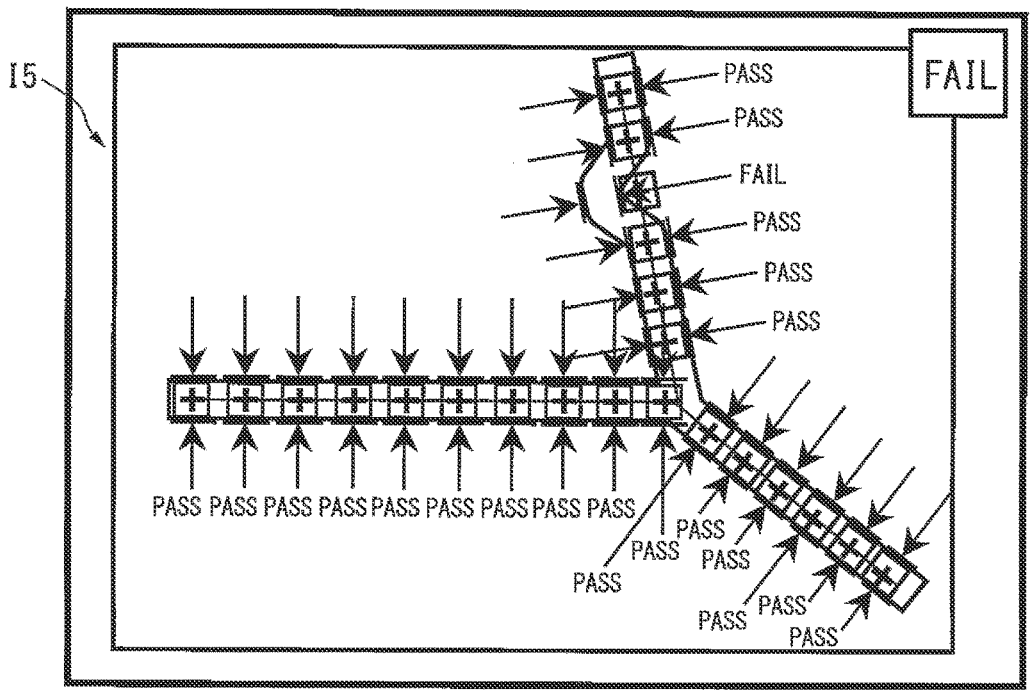
FIG. 41b shows an example wherein a comprehensive judgment is "FAIL" in the fifth working example, since a portion of sealing agent is serpentine.
Figure 41C:
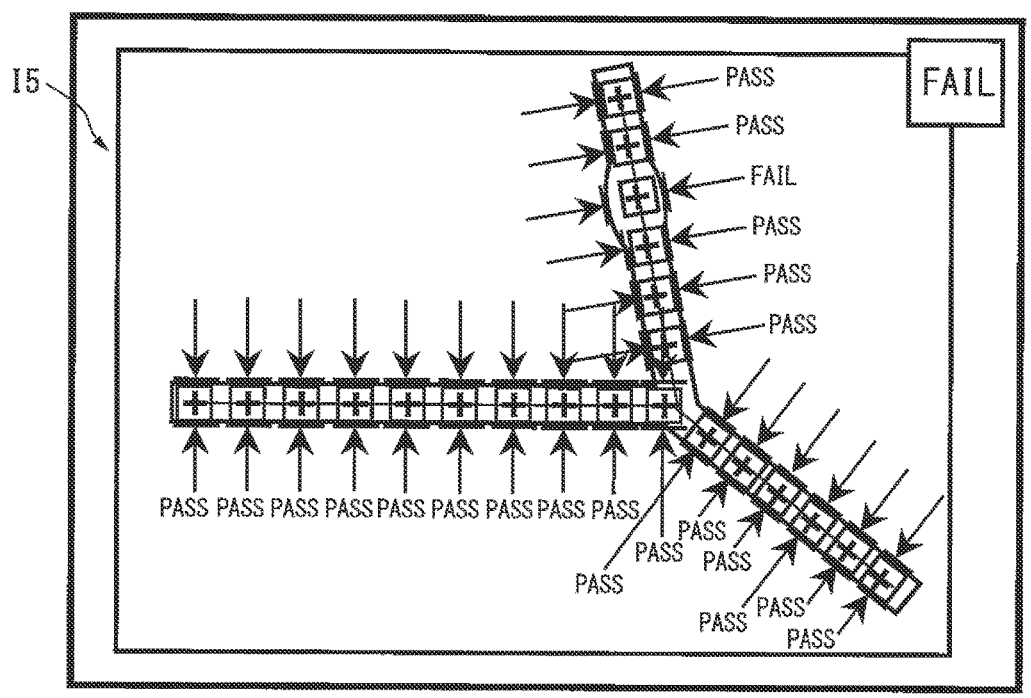
FIG. 41c shows an example wherein a comprehensive judgment is "FAIL" in the fifth working example, since a portion of sealing agent has a wider width.

FIG. 40 shows an example of an image displayed on display device 1300, wherein all of the inspection points are judged as "PASS" and the comprehensive judgment is also "PASS." In other words, FIG. 40 shows the inspection result when sealing agent 40 is appropriately applied to inspection object W4 in a predetermined width and in a seamless manner. On the other hand, FIGS. 41a to 41c show examples of an image displayed on display device 1300, wherein at least one of the inspection points is judged as "FAIL." Concretely, FIG. 41a shows an example wherein adhesive agent 40 applied to inspection object W4 has an incision, FIG. 41b shows an example wherein adhesive agent 40 partially has a serpentine shape, and FIG. 41c shows an example wherein a portion of adhesive agent 40 has a width than a predetermined width. In any example, the inspection result of the inspection point including a deficiency is judged as "FAIL," and the comprehensive judgment is also "FAIL."

According to the present invention, by means of simple teaching operation, a line pattern having an arbitrary shape including a branch point, etc., may be determined as a portion to be inspected, whereby the elongated portion to be inspected can be inspected over the entire length thereof with a certain level of quality. An interval of each inspection point may be constant, based on a distance which is experimentally or empirically determined. Even if the contrast of the line pattern is unclear, an appropriate portion may be determined as a portion to be inspected. Further, in relation to one taught line pattern, the appearance inspection based on a plurality of factors such as the brightness, the area, the width and the contrast may be simultaneously executed.

While the invention has been described with reference to specific embodiments chosen for the purpose of illustration, it should be apparent that numerous modifications could be made thereto, by a person skilled in the art, without departing from the basic concept and scope of the invention.

The invention claimed is:

1. An appearance inspection device for inspecting an appearance of an inspection object, said appearance inspection device comprising:
   an image storing part which stores
      a first image obtained by capturing a reference object corresponding to the inspection object, and
      a second image obtained by capturing the inspection object;
   a teaching part which
      based on an input by an operator, teaches, on the first image, a portion to be inspected of the inspection object as a reference inspection line,
      defines a reference inspection region associated with a single reference inspection point on the reference inspection line,
      determines an inspection factor inspected within the reference inspection region, and
      determines a judgment condition for judging as to whether a result of inspection based on the inspection factor passes or fails;
   a teaching factor storing part which stores
      a position and a shape of the reference inspection line,
      a position of the single reference inspection point,
      an inspection point distance,
      a position and a size of the reference inspection region,
      the inspection factor, and
      the judgment condition; and
   an inspecting part which
      overlaps the reference inspection line on the second image as an actual inspection line,
      generates a plurality of discrete inspection points, distinct from the single reference inspection point, on the actual inspection line, by
         determining a number of the inspection points to be generated by dividing a total length of the actual inspection line by the inspection point distance stored in the teaching factor storing part, and
         arranging the determined number of the inspection points on the actual inspection line at the inspection point distance from each other,
      generates a plurality of inspection regions, distinct from the reference inspection region, in relation to the plurality of discrete inspection points, wherein
         each inspection point among the plurality of discrete inspection points corresponds to an inspection region among the plurality of inspection regions so that a positional relationship between the corresponding inspection point and inspection region is the same as a positional relationship between the single reference inspection point and the reference inspection region, and
         the same positional relationship between the single reference inspection point and the reference inspection region is used to generate the plurality of inspection regions,
      inspects each inspection region among the plurality of generated inspection regions based on the inspection factor,
      judges as to whether each inspection point among the plurality of discrete inspection points passes or fails based on the judgment condition and a result of inspection of the corresponding inspection region among the plurality of generated inspection regions, and
      comprehensively judges as to whether the inspection object passes or fails based on a result of judgment of each inspection point among the plurality of discrete inspection points,
   wherein the teaching part defines the reference inspection region associated with said single reference inspection point on the reference inspection line before the inspecting part overlaps the reference inspection line on the second image as the actual inspection line.

2. The appearance inspection device as set forth in claim 1, wherein the teaching part teaches the reference inspection line using one of a polygonal line, an arc, a circle and a free curve, or a combination thereof.

3. The appearance inspection device as set forth in claim 1, wherein
   the teaching factor storing part stores a position of the reference object within the first image, and
   the inspecting part
      moves the actual inspection line so that a position of the moved actual inspection line relative to a position of the inspection object within the second image is the same as a position of the reference inspection line relative to the reference object stored in the teaching factor storing part, and thereafter
      generates the plurality of discrete inspection points.

4. The appearance inspection device as set forth in claim 3, wherein
   after
      the teaching part
         teaches the reference inspection line, and
         defines the reference inspection region, and
      the teaching factor storing part stores
         a position of the reference object within the first image,
         the position and shape of the reference inspection line,
         the position of the single reference inspection point, and
         the position and size of the reference inspection region,
   the inspecting part
      overlaps the reference inspection line on the second image as the actual inspection line, then
      moves the actual inspection line so that a position of the moved actual inspection line relative to a position of the inspection object within the second image is the same as a position of the reference inspection line relative to the reference object stored in the teaching factor storing part, then
      generates the plurality of discrete inspection points on the moved actual inspection line, then
      generates the plurality of inspection regions in relation to the plurality of discrete inspection points, then
      inspects each inspection region among the plurality of generated inspection regions based on the inspection factor, and then
      judges as to whether each inspection point among the plurality of discrete inspection points passes or fails, and comprehensively judges as to whether the inspection object passes or fails.

5. The appearance inspection device as set forth in claim 1, wherein
   the teaching part
      defines a plurality of reference inspection regions associated with the single reference inspection point, and
      determines an inspection factor in relation to each reference inspection region among the plurality of reference inspection regions, and the inspecting part
    inspects a plurality of inspection regions generated corresponding to the plurality of reference inspection regions based on the inspection factor, and
    applies the judgment condition to a result of inspection in each inspection region among the plurality of inspection regions so as to obtain the result of judgment of each inspection point among the plurality of discrete inspection points.

6. The appearance inspection device as set forth in claim 1, wherein the plurality of discrete inspection points are generated, at the inspection point distance, on the actual inspection line overlapped with the second image.

7. The appearance inspection device as set forth in claim 1, wherein the reference inspection line is not on a contour of the reference object.

8. The appearance inspection device as set forth in claim 1, wherein the teaching part defines only said single reference inspection point on the reference inspection line.

9. The appearance inspection device as set forth in claim 1, wherein
after
    the teaching part
        teaches the reference inspection line, and
        defines the reference inspection region, and
    the teaching factor storing part stores
        the position and shape of the reference inspection line,
        the position of the single reference inspection point, and
        the position and size of the reference inspection region,
    the inspecting part
        overlaps the reference inspection line on the second image as the actual inspection line, then
        generates the plurality of discrete inspection points on the actual inspection line, then
        generates the plurality of inspection regions in relation to the plurality of discrete inspection points, then
        inspects each inspection region among the plurality of generated inspection regions based on the inspection factor, and then
        judges as to whether each inspection point among the plurality of discrete inspection points passes or fails, and comprehensively judges as to whether the inspection object passes or fails.

10. An appearance inspection method of inspecting an appearance of an inspection object, said appearance inspection method comprising:
    an image storing process of storing
        a first image obtained by capturing a reference object corresponding to the inspection object, and
        a second image obtained by capturing the inspection object;
    a teaching process comprising
        based on an input by an operator, teaching, on the first image, a portion to be inspected of the inspection object as a reference inspection line,
        defining a reference inspection region associated with a single reference inspection point on the reference inspection line,
        determining an inspection factor inspected within the reference inspection region, and
        determining a judgment condition for judging as to whether a result of inspection based on the inspection factor passes or fails;
    a teaching factor storing process of storing
        a position and a shape of the reference inspection line,
        a position of the single reference inspection point,
        an inspection point distance,
        a position and a size of the reference inspection region,
        the inspection factor, and
        the judgment condition; and
    an inspecting process comprising
        overlapping the reference inspection line on the second image as an actual inspection line,
        generating a plurality of discrete inspection points, distinct from the single reference inspection point, on the actual inspection line, by
            determining a number of the inspection points to be generated by dividing a total length of the actual inspection line by the inspection point distance stored in the teaching factor storing part, and
            arranging the determined number of the inspection points on the actual inspection line at the inspection point distance from each other,
        generating a plurality of inspection regions, distinct from the reference inspection region, in relation to the plurality of discrete inspection points, wherein
            each inspection point among the plurality of discrete inspection points corresponds to an inspection region among the plurality of inspection regions so that a positional relationship between the corresponding inspection point and inspection region is the same as a positional relationship between the single reference inspection point and the reference inspection region, and
            the same positional relationship between the single reference inspection point and the reference inspection region is used to generate the plurality of inspection regions,
        inspecting each inspection region among the plurality of generated inspection regions based on the inspection factor,
        judging as to whether each inspection point among the plurality of discrete inspection points passes or fails based on the judgment condition and a result of said inspecting the corresponding inspection region among the plurality of generated inspection regions, and
        comprehensively judging as to whether the inspection object passes or fails based on a result of judgment of each inspection point among the plurality of discrete inspection points,
    wherein said defining the reference inspection region associated with said single reference inspection point on the reference inspection line is performed before said overlapping the reference inspection line on the second image as the actual inspection line.

11. The appearance inspection method as set forth in claim 10, wherein said teaching the reference inspection line uses one of a polygonal line, an arc, a circle and a free curve, or a combination thereof.

12. The appearance inspection method as set forth in claim 10, wherein
    the teaching factor storing process includes storing a position of the reference object within the first image, and
    the inspecting process includes
        moving the actual inspection line so that a position of the moved actual inspection line relative to a position of the inspection object within the second image is the same as a position of the reference inspection line relative to the reference object stored in the teaching factor storing process, and after said moving, generating the plurality of discrete inspection points.

13. The appearance inspection method as set forth in claim 12, wherein the teaching factor storing process includes storing a position of the reference object within the first image, and after said teaching the reference inspection line,
said defining the reference inspection region, and
said storing the position of the reference object within the first image, the position and shape of the reference inspection line, the position of the single reference inspection point, and the position and size of the reference inspection region, said inspecting process is performed in an order of said overlapping the reference inspection line on the second image as the actual inspection line, then moving the actual inspection line so that a position of the moved actual inspection line relative to a position of the inspection object within the second image is the same as a position of the reference inspection line relative to the reference object stored in the teaching factor storing process, then said generating the plurality of discrete inspection points on the actual inspection line, then said generating the plurality of inspection regions in relation to the plurality of discrete inspection points, then said inspecting each inspection region among the plurality of generated inspection regions, and then said judging as to whether each inspection point among the plurality of discrete inspection points passes or fails, and said comprehensively judging as to whether the inspection object passes or fails.

14. The appearance inspection method as set forth in claim 10, wherein the teaching process includes defining a plurality of reference inspection regions associated with the single reference inspection point, and determining an inspection factor in relation to each reference inspection region among the plurality of reference inspection regions, and the inspecting process includes inspecting a plurality of inspection regions generated corresponding to the plurality of reference inspection regions based on the inspection factor, and applying the judgment condition to a result of inspection in each inspection region among the plurality of inspection regions so as to obtain the result of judgment of each inspection point among the plurality of discrete inspection points.

15. The appearance inspection method as set forth in claim 10, wherein the plurality of discrete inspection points are generated, at the inspection point distance, on the actual inspection line overlapped with the second image.

16. The appearance inspection method as set forth in claim 10, wherein the reference inspection line is not on a contour of the reference object.

17. The appearance inspection method as set forth in claim 10, wherein, in the teaching process, only said single reference inspection point is defined on the reference inspection line.

18. The appearance inspection method as set forth in claim 10, wherein after said teaching the reference inspection line,
said defining the reference inspection region, and
said storing the position and shape of the reference inspection line, the position of the single reference inspection point, and the position and size of the reference inspection region, said inspecting process is performed in an order of said overlapping the reference inspection line on the second image as the actual inspection line, then said generating the plurality of discrete inspection points on the actual inspection line, then said generating the plurality of inspection regions in relation to the plurality of discrete inspection points, then said inspecting each inspection region among the plurality of generated inspection regions, and then said judging as to whether each inspection point among the plurality of discrete inspection points passes or fails, and said comprehensively judging as to whether the inspection object passes or fails.

* * * * *